US012578353B2

(12) United States Patent
    Webb

(10) Patent No.: US 12,578,353 B2
(45) Date of Patent: Mar. 17, 2026

(54) ROBOTIC SYSTEM AND METHOD FOR PRECISE ORGAN EXCISION TECHNOLOGY

(71) Applicant: Vitality Robotics Inc., Morrisville, NC (US)

(72) Inventor: Joe Webb, Morrisville, NC (US)

(73) Assignee: VITALITY ROBOTICS INC., Morrisville, NC (US)

( * ) Notice: Subject to any disclaimer, the term of this patent is extended or adjusted under 35 U.S.C. 154(b) by 635 days.

(21) Appl. No.: 17/985,342

(22) Filed: Nov. 11, 2022

(65) Prior Publication Data

US 2023/0142440 A1 May 11, 2023

Related U.S. Application Data

(60) Provisional application No. 63/278,478, filed on Nov. 11, 2021.

(51) Int. Cl.
    *G01N 35/00* (2006.01)
    *A61B 34/32* (2016.01)
    (Continued)

(52) U.S. Cl.
    CPC ......... *G01N 35/0099* (2013.01); *A61B 34/32* (2016.02); *G01N 1/31* (2013.01);
    (Continued)

(58) Field of Classification Search
    CPC . B25J 9/0084; B25J 15/04; B25J 19/02; B25J 21/00; A61B 2034/2055;
    (Continued)

(56) References Cited

U.S. PATENT DOCUMENTS

| | | | |
|---|---|---|---|
| 2008/0099020 A1* | 5/2008 | Nelson | A01K 1/031 |
| | | | 128/205.26 |
| 2008/0190953 A1* | 8/2008 | Mallett | B07C 7/005 |
| | | | 221/13 |

(Continued)

FOREIGN PATENT DOCUMENTS

| | | | | |
|---|---|---|---|---|
| JP | 2006081994 A | * | 3/2006 | C12M 41/14 |

OTHER PUBLICATIONS

JP-2006081994-A—translation (Year: 2006).*

*Primary Examiner* — Abby Lin
*Assistant Examiner* — Renee LaRose
(74) *Attorney, Agent, or Firm* — Eckert Seamans Cherin & Mellot, LLC

(57) ABSTRACT

Methods and systems for automating surgical procedures in model organisms. The system includes a user input panel, a trained computer vision system, a server, and articulated robotic arm. The system may further include an analytical scale, an anesthesia chamber, a tube labeling system, a tissue freezing system, and a biohazard waste disposal system. The computer vision system communicates with the robotic arm to coordinate tissue collections and common research procedures such as injections via recognition models related to detection, identification, localization, and classification. The central server provides rapid synchronization of data between the local machine and a cloud account system for real-time data analytics. The anesthesia chamber provides standardized administration of anesthesia, the sample labeling system provides 2D barcoded labels according to user input, and the tissue freezing and waste disposal systems enable storage of samples and removal of carcasses following tissue collection, fully automating the necropsy.

21 Claims, 15 Drawing Sheets

(51) Int. Cl.
  *G01N 1/31*            (2006.01)
  *G01N 35/02*           (2006.01)
(52) U.S. Cl.
  CPC . *G01N 35/00732* (2013.01); *G01N 35/00871*
          (2013.01); *G01N 35/02* (2013.01); *G01N*
          *2035/00306* (2013.01); *G01N 2035/00316*
          (2013.01); *G01N 2035/00445* (2013.01); *G01N*
          *2035/00831* (2013.01)
(58) Field of Classification Search
  CPC ....... A61B 90/361; A61B 90/94; A61B 90/96;
              A61B 2090/064; A61M 16/009; A61M
                16/01; A61M 16/18; A61M 2250/00
  See application file for complete search history.

(56) References Cited

U.S. PATENT DOCUMENTS

| | | | |
|---|---|---|---|
| 2016/0058517 A1 | 3/2016 | Kim et al. | |
| 2018/0151012 A1* | 5/2018 | Kuraoka | F16P 3/08 |
| 2020/0046439 A1* | 2/2020 | Tekiela | A61B 34/74 |
| 2020/0188043 A1* | 6/2020 | Yu | A61G 13/08 |
| 2020/0338309 A1* | 10/2020 | Kopperschmidt | A61M 25/0116 |
| 2020/0383734 A1* | 12/2020 | Dahdouh | A61B 34/30 |
| 2021/0283565 A1* | 9/2021 | Gerlinghaus | C12M 37/00 |
| 2024/0336429 A1* | 10/2024 | Clancy | B65G 1/1378 |

* cited by examiner

Organs Present: True

Species Labeled: Mouse

Species Classification: Mouse

Image ID: ABC-123-0001567-2021

Organs Labeled: Intestines, Liver, Bladder

Organs Detected: Intestines, Liver, Bladder

ROBOTIC SYSTEM AND METHOD FOR PRECISE ORGAN EXCISION TECHNOLOGY

CROSS-REFERENCE TO RELATED APPLICATIONS

The present application claims the benefit under 35 U.S.C. § 119(e) of prior U.S. Provisional Application Ser. No. 63/278,478, filed Nov. 11, 2021, the entire contents of which is incorporated herein by reference.

FIELD OF INVENTION

The present disclosure is primarily related to scientific laboratory automation equipment systems, and more specifically to automated systems and methods for administering anesthesia, collecting tissues and samples from model organisms, collecting data, and organizing the tissues and samples into tubes, racks, and liquid nitrogen canisters.

BACKGROUND

In scientific research facilities, such as academic laboratories or industrial pharmaceutical companies, preclinical research is primarily conducted on model organisms such as rodents, birds, amphibians, and worms to study how small molecules, vaccines, or therapeutic treatments affect disease. Each study examining how these therapies function on a molecular level or how organs respond to treatment require the precise excision of various tissues, such as the kidney while studying kidney disease or the ovaries while studying poly-cystic ovarian syndrome.

In an academic laboratory conducting studies with animals, scientists often collect as many tissues as possible to archive these bio samples for future studies or examine the effect of drugs across numerous tissues. When scientists need to conduct one of these studies, they begin by carefully creating a study design to test their hypothesis, followed by administering dietary treatments, oral gavage, IV, IP, subcutaneous injections, or other miscellaneous methods for drug delivery. After successfully completing the study design, scientists may spend hours meticulously labeling sample tubes/boxes and organizing tissue cassettes for specimen collection during a surgical procedure for collecting tissues, i.e., during a necropsy.

During necropsy, animals are typically given anesthesia, followed by euthanasia in accordance with their local advisory board protocols. Typically, animals are injected with ketamine/xylazine or other barbiturate drugs to anesthetize the animal or are subjected to gas anesthesia such as Isoflurane for short term anesthesia. Once the animals are anesthetized, the scientists may perform two methods of euthanasia such as exsanguination (removal of the blood), decapitation, cervical dislocation, or removal of vital internal organs in accordance with the Institutional Animal Care and Use Committee to ensure that animals used in research receive humane care.

There are several common problems associated with administering anesthesia in the research setting including: 1) flowrate standardization—research personnel might administer different flow rates of oxygen-to-isoflurane resulting in drastically different levels of anesthetization between animals in the same study; 2) lack of training—to properly set up anesthesia equipment requires training by DVM or PHD staff to allow for adequate functioning of the equipment; 3) differences between users—in the academic realm there are often new students performing these tasks every semester, so there are typically large variations in the location that untrained students inject animals, sometimes resulting in unwanted premature death prior to euthanasia; and 4) injection volume differences—when utilizing common injection anesthesia cocktails such as ketamine/xylazine, each animal requires a different volume to provide the same dosage, requiring different volumes and sometimes multiple injections.

After euthanasia, common metabolic studies may include excision of specific organs according to their research study design. For example, the kidney may be removed when the animal is part of a study examining kidney disease. After removal from the body, the kidney may be transferred to a piece of weigh paper and placed on an analytical scale to weigh the organ. The tissue weights are recorded manually with pen and paper, and the tissues are then 1) placed into a labeled tissue cassette and subsequently submerged in formalin; 2) placed into a labeled small microtube and immediately "snap" frozen in liquid nitrogen; or 3) placed into a labeled small microtube with a small volume of chemicals such as RnaLater© to preserve mRNA. Other studies might perform a process called perfusion to remove blood from the organs, such as by slicing open the atrium of the heart and pumping fluid through the circulatory system. Immediately following total perfusion, the above processes are completed followed by fixation of the tissue in a formalin buffer for tissue histology.

One fundamental problem with this process arises either during or prior to necropsy, where scientists must individually label tubes for each specimen they intend to collect from each animal. Some scientific studies can be conducted on anywhere from 3 to 50 rodents per treatment group, where it is common to have between 2 to 10 distinct treatment groups. If a scientist is going to perform multiple types of assays with each tissue that is collected, they could require 3 to 6 separate labeling workflows for each tissue (blood tubes, tissue cassettes, protein tubes, RNA tubes, frozen tissue, biohazard bags, weigh paper, etc.). Thus, this very manual process can require numerous hours of preparation before the necropsy and is sometimes performed during the surgical procedure, thus greatly slowing the procedure. Academic studies often only collect enough tissues for their current study, while many industry laboratories collect nearly every organ/tissue sample available for future studies, further increasing the necessary labeling workflow for necropsies.

Due to the very time-consuming nature of this sample collection process, several automated labeling tools have been created, such as the SCINOMIX print solo systems for labeling tubes of various sizes individually, or the TubeWriter™ for labeling large numbers of identical tubes. However, all these types of automated tube labeling machines require connection to a PC or for a user to type/predefine the contents for each label. Other approaches such as the IntelliXmark™ printers provide large desktop solutions for high throughput laboratories to label large numbers of tubes. However, none of these automated solutions currently provide labeling tools for marking tissue cassettes in addition to labeling other types of tubes such as 1.5 mL microfuge tubes, 3 mL blood tubes, or 8 mL blood tubes.

Two primary objections to automating these surgical tasks are: 1) the perceived cost is too expensive, and 2) the automation would not perform surgical tasks as precisely as a trained scientist or research veterinarian. As such, most businesses to date rely primarily on manual labor to perform these tasks, sometimes requiring up to 4 scientists each spending 40 hours of work performing necropsies on rodents for each scientific study, and additional time for labeling tubes.

Accordingly, a solution that can perform sample preparation, collection, and storage at a similar or greater level of accuracy as a trained scientist would allow these facilities to utilize such devices for surgical tasks requiring very precise movements. Additionally, since most of the current automation solutions require changes in the infrastructure, providing a benchtop device would allow for a reduced anticipated startup cost. As workers can spend less time performing necropsies, an additional cost savings would be expected, allowing the scientists to spend more time on their core work rather than executing repetitive surgical tasks.

SUMMARY

The presently disclosed invention overcomes most if not all shortcomings of the prior art laboratory automation solutions, devices, and methods for sample labeling, sample handling, and animal anesthesia. The presently disclosed robotic systems provide modular system for automating necropsies and performing common preclinical research techniques such as injections and tissue collection. The presently disclosed systems and methods allow for existing scientific laboratories to utilize both robotic surgical applications and manual surgeries simultaneously, thus allowing trained staff to spend less time on repetitive surgical tasks.

Accordingly, and briefly stated, the present invention provides a system for automated surgical procedures including a processor and memory, an articulated robotic arm comprising an end effector, a plurality of sensors, and a surgical platform. The processor may be coupled to the plurality of sensors and the articulated robotic arm, and one or more of the plurality of sensors provide signals related to detection and identification of features of a surgical specimen. Moreover, the memory stores program instructions executable by the processor to process data received from the plurality of sensors and output control signals to the articulated robotic arm to perform an automated surgical procedure.

The system may include a remote communication interface. As such, the system may be configured to send data collected during the automated surgical procedure to a remote server, receive data related to the automated surgical procedure from the remote server, store program instructions to the memory received from the remote server, or any combination thereof. The remote server may be a cloud-based server or a server on a local area network.

The end effector may be a surgical instrument or a cleaning instrument. The articulated robotic arm may be configured to autonomously exchange the end effector for a second end effector, such as by removing the end effector and inserting the second end effector. Alternatively, or additionally, the end effector may comprise multiple surgical and/or cleaning instruments that may be individually moved into a working position.

The surgical platform may include a breakaway plate configured to open to a collection chamber positioned below. The collection chamber may be configured as part of a drawer on the system that collects waste into individual closable containers when the breakaway plate opens.

The plurality of sensors may include any combination of a color camera, 3D camera, LIDAR system, infrared sensor, magnetic sensor, structured light sensor, proximity sensor, force sensor, and time-of-flight sensor. The plurality of sensors may further include any combination of a temperature sensor, humidity sensor, pressure sensor, gas sensor, and combinations thereof. The plurality of sensors may include any combination of a color camera, 3D camera, LIDAR system, infrared sensor, magnetic sensor, structured light sensor, proximity sensor, force sensor, and time-of-flight sensor, and any combination of a temperature sensor, humidity sensor, pressure sensor, and gas sensor.

The articulated robotic arm, the plurality of sensors, and the surgical platform may be positioned within an interior of a housing having an inner shell, an outer shell, and an access door, wherein the articulated robotic arm may be attached to a wall of the housing on the inner shell. Access to the interior of the housing may be via the access door, and wherein the processor outputs control signals to lock the access door during the automated surgical procedure.

The system may include an anesthesia unit comprising a positive air flow chamber, e.g., induction chamber, an anesthetic supply, and a flow regulator in fluid communication with the anesthetic supply and the positive air flow chamber. The anesthesia unit may provide anesthesia sufficient to anesthetize or euthanize the model animal. The flow regulator may comprise a flow rate detector and solenoid controllers. The processor may be coupled to the flow regulator and output control signals to the solenoid controllers. The memory may store program instructions executable by the processor to process data received from the flow rate detector and the plurality of sensors to track progress of the automated surgical procedure, to change a flow rate of the anesthetic from the anesthetic supply to the induction chamber, or both.

The system may include a conveyor system to move the surgical specimen from the positive air flow chamber to the surgical platform.

The system may include a sample handling unit comprising a tube labeling system and a tube manipulation robot. The tube manipulation robot may be configured to collect sample tubes from a tube container, place the sample tubes into position within the tube labeling system to provide a labeled sample tube, and position the labeled sample tube for collection of a sample from the surgical specimen. Moreover, the tube labeling system may be configured to mark the sample tube with a barcode, text comprising a sample name, a sample collection date, a sample collection time, a protocol name, a protocol number, a user identity, or any combination thereof. The sample tubes may be of varied size and configuration.

The sample handling unit may include a sample storage area configured as a drawer on the system. A temperature of the sample storage area may be above or below ambient. When below ambient, such as below $-20°$ C., the sample handling unit may include a freezing system comprising a removable liquid nitrogen canister.

The freezing system may further include an integrated liquid nitrogen refilling and dispensing station configured to provide refill of liquid nitrogen. The freezing system may include a freezer unit in place of a liquid nitrogen rapid freezing station which may comprise multiple freezer units at a variety of different temperature ranges.

One or more of the plurality of sensors may comprise a camera configured to acquire images. Either the camera or the processor may use the images to generate image data representing at least a part of the image and may transmit the image data in real time to the processor, the memory, the remote server (i.e., local or cloud-based), or any combination thereof. The processor is generally configured to determine a real-time spatial position of the end effector of the articulated robotic arm based on the image data. Moreover, the processor may direct real-time positions of the articulated robotic arm and the end effector attached thereto during the surgical procedure based on machine learning applied to datasets of previously performed surgical procedures.

The end effector may comprise a calibration location, and the processor may be configured to perform a calibration of the real-time spatial position of the end effector.

BRIEF DESCRIPTION OF THE DRAWINGS

Aspects, features, benefits, and advantages of the embodiments herein may be apparent with regard to the following descriptions, appended claims, and accompanying drawings. In the following figures, like numerals represent like features in the various views. It is to be noted that the features and the components in these drawings, illustrating the views of embodiments of the present invention, unless stated to be otherwise, are not necessarily drawn to scale. The illustrations in the following drawings were not meant to be limiting, whereas other embodiments may be utilized, and other changes may be made without departing from the spirit or the scope of the subject matter presented herein.

FIGS. 10A-10F depict application of custom algorithms for image analysis to identify specific surgical landmarks to detect organs according to aspects of the present disclosure, wherein FIG. 10A is an image of a model animal captured by the disclosed system, FIGS. 10B-10D depict identification of features in the image of FIG. 10A by the custom algorithms of the present disclosure, and FIGS. 10E and 10F depict edge detection in the image of FIG. 10A by the custom algorithms of the present disclosure.

FIGS. 12A and 12B provide a demonstration of the presently disclosed user interface for labeling custom training data on the edge device, wherein FIG. 12A depicts an image of a model animal captured by the disclosed system, and FIG. 12B depicts labeling of organs and/or tissues found in FIG. 12A via a customized training process.

DETAILED DESCRIPTION

Figure 1A:
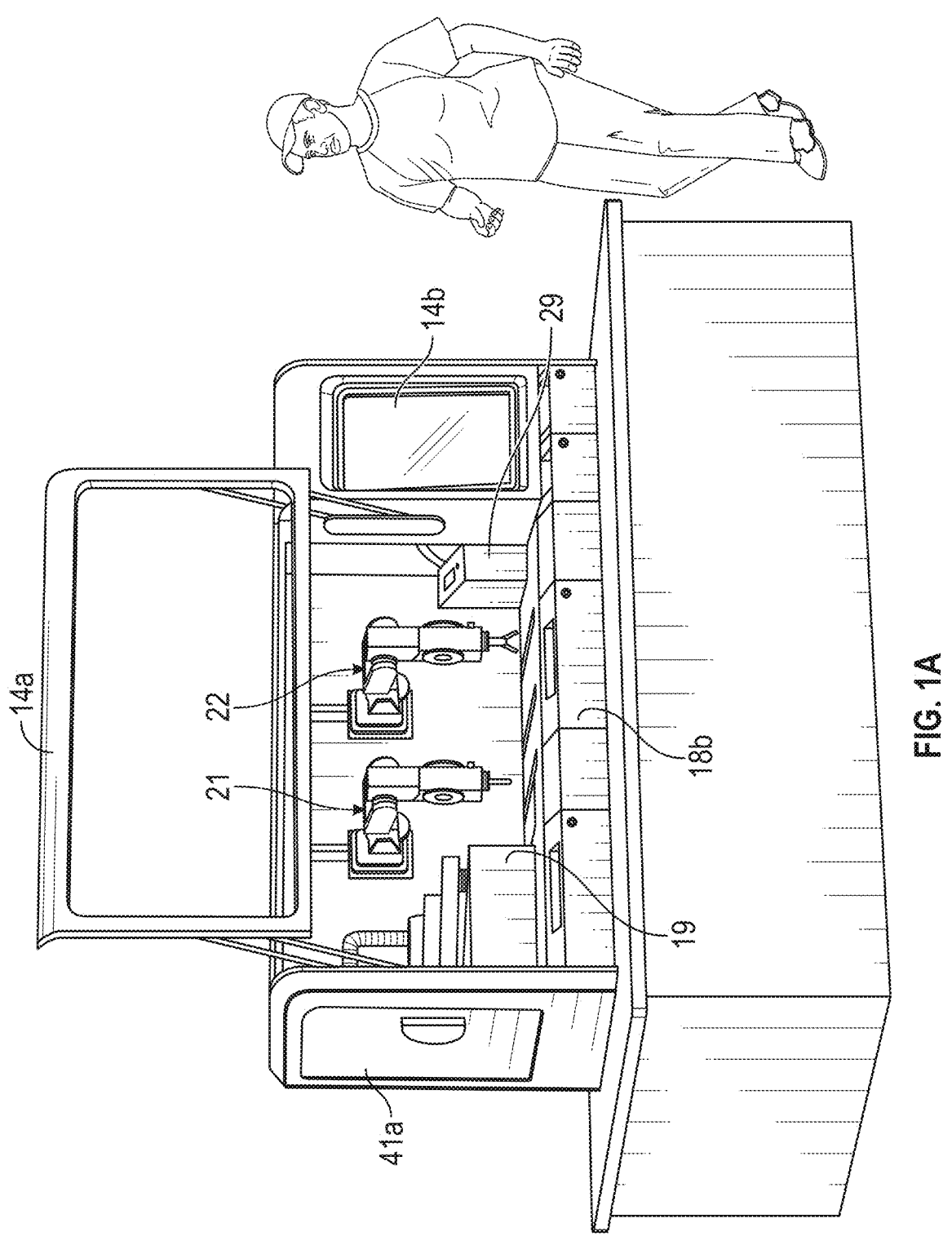
FIG. 1A illustrates a perspective view of a modular surgical system according to aspects of the present disclosure.

The presently disclosed robotic systems and methods solve several aspects of animal necropsies that are challenging and remain unsolved in the prior art. Specifically, the disclosed systems enable a robotic arm with a high degree of freedom to manipulate common research tools to perform tissue excision, collection, and storage. Each of these systems include one or more components that are individually configured to automate specific tasks related to the tissue excision, collection, and storage, such as small animal anesthesia, small animal surgery (e.g., tissue excision), and sample tube labeling and storage.

Accordingly, a system may include a plurality of sensors, a remote communication interface, a memory configuration, a processing component, one or more machine learning compute nodes, an articulated manipulator arm, a visual coordination system, a sample handling system, a freezing system, a biohazard waste system, and a human interface system.

Before describing the systems and methods disclosed herein, certain terms and abbreviations will first be discussed and/or defined.
Abbreviations and Definitions As used in the specification including the appended claims, the singular forms "a," "an," and "the" include the plural, and reference to a particular numerical value includes at least that particular value, unless the context clearly dictates otherwise (i.e., a plurality of). As example, "a" processor may comprise one or more processors, "an" end effector may comprise one or more end effectors, "the" gas cylinder may comprise one or more gas cylinders, and the like, while "the plurality of" sensors comprises two or more sensors.

The word "comprising" and forms of the word "comprising", as used in the specification including the appended claims, does not limit the present invention to exclude any variants or additions. Additionally, although the present invention has been described in terms of "comprising", the devices, assemblies, and methods detailed herein may also be described as consisting essentially of or consisting of. For example, while the invention has been described in terms of a system comprising multiple components, a system 'consisting essentially of' or 'consisting of' the same components is also within the present scope, wherein additional components that are not relevant to the functionality of the system may be included.

The use of "or" means "and/or" unless specifically stated otherwise.

As used herein, the term "substantially" may be taken to represent the inherent degree of uncertainty that may be attributed to any quantitative comparison, value, measurement, or other representation. Thus, the term substantially may mean an amount of generally at least about 80%, about 90%, about 95%, about 98%, or even about 99% of the listed comparison, value, measurement, or other representation.

Various aspects of the systems and methods disclosed herein may be illustrated by describing components that are coupled, attached, and/or joined together. The terms "coupled", "attached", and/or "joined" are used interchangeably in this disclosure to indicate either a direct connection between two components or, where appropriate, an indirect connection to one another component through intervening or intermediate components. In contrast, when a component is referred to as being "directly coupled", "directly attached", and/or "directly joined" to another component, there are no intervening elements or components.

Relative terms such as "lower" or "bottom" and "upper" or "top" are used herein to describe one element's relationship to another element illustrated in the drawings. It may be understood that relative terms are intended to encompass different orientations of aspects of the system in addition to the orientation depicted in the drawings. By way of example, if aspects of the system shown in the drawings are turned over, elements described as being on the "bottom" side of the other elements would then be oriented on the "top" side of the other elements as shown in the relevant drawing. The term "bottom" can therefore encompass both an orientation of "bottom" and "top" depending on the particular orientation of the drawing.

Other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and appended claims are approximations that may vary depending upon at least the substrate used, the type and form of touch sensitive and display surfaces, and the size of the assembly or device comprising the assembly. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

"Including" and like terms should be understood to mean "including, but not limited to". When ranges are given, any endpoints of those ranges and/or numbers within those ranges can be combined within the scope of the present invention.

As used herein, the term "digital information" may be understood to include any textual or graphical information that may be conveyed by a processor, such as a central processing unit (CPU) or graphical processing unit (GPU), and displayed on an output device, such as a computer display or screen, of the presently disclosed system.

The terms "storage" and "data storage" and "memory," when used in the context of a computer system or method, may be used interchangeably and may be taken to indicate both transient and permanent storage (i.e., on a non-volatile memory hardware device) of data on a computer.

The term "surgical instrument" is used herein to indicate a surgical tool adapted for performing surgery onto a tissue such as a grasper, a suture grasper, a cutter, a sealer, a stapler, a clip applier, a dissector, scissors, shears, a suction instrument, a clamp instrument, an electrode, a coagulation device, a curette, ablators, scalpels, a needle holder, a needle driver, a spatula, forceps, a biopsy and retractor instrument, or a combination thereof.

The term "sensor" is used herein to indicate a device that detects or measures a physical property and records, indicates, or otherwise responds to it. Exemplary sensors include at least color cameras, 3D cameras, LIDAR systems, infrared sensors, time-of-flight sensors, magnetic sensors, force sensors, pressure sensors, structured light sensors, temperature sensors, humidity sensors, pressure sensors, gas sensors, and any other sensors known in the art that are useful for robotic manipulation and calibration, climate control, automated surgeries, and the like.

As used herein, the term "edge device" may be understood to include a device that provides an entry point into enterprise or service provider core networks. Examples include routers, routing switches, integrated access devices, multiplexers, and a variety of metropolitan area network and wide area network access devices The term "real time" is herein used to mean the time it requires the computer to receive and process constantly changing data, optionally in combination with other data such as predetermined data, reference data, estimated data, which may be non-real time data such as constant data or data changing with a frequency of above 1 minute to return the real time information to the user. "Real time" may include a short delay, such as up to 5 seconds, preferably within 1 second, more preferably within 0.1 second of an occurrence.

As used herein, the term "system" may refer to individual units of the disclosed invention, such as a surgical unit comprising an articulated robotic arm and a surgical platform, a sample handling unit comprising a tube labeling component and a tube/sample freezing and/or storage component, an anesthesia unit comprising an anesthesia chamber and anesthesia supply, and a waste removal unit comprising means for removal of solid and liquid wastes. Other components are possible, certain of which are described herein, as are additional units. Moreover, the term system may also be understood to refer to a group of units or components thereof. Systems of the present invention further include software products and databases useful for the visualization and localization of relevant tissues and organs of a surgical specimen, e.g., rat, mouse, and the like, for the purpose of informing a robotic surgery. Additional systems of the present invention include software products to inform specific robotic surgery protocols, including surgical procedures and sample preparation/storage.

The inventions detailed in this disclosure are not limited to the specific devices, methods, processes, elements, or parameters described and/or shown herein and the terminology used herein is for the purpose of describing particular embodiments and is by way of example only and not intended to be limiting of the claimed invention. Any and all patents and other publications identified in this specification are incorporated by reference as though fully set forth herein.

In the following description, certain details are set forth in order to provide a better understanding of various embodiments of the presently disclosed robotic systems and methods. However, one skilled in the art may understand that these embodiments may be practiced without these details and/or in the absence of any details not described herein. In other instances, well-known structures, methods, and/or techniques associated with methods of practicing the various embodiments may not be shown or described in detail to avoid unnecessarily obscuring descriptions of other details of the various embodiments.

Components of the Disclosed Systems

The present disclosure provides systems and methods for automating procedures such as: administration of anesthesia to anesthetize or euthanize, surgery on model organisms, collection of tissues and samples from model organisms, acceptance of data regarding samples to be collected and stored, organization of the tissues and samples into tubes, racks, and liquid nitrogen canisters, and collection of data during each of these procedures. These procedures utilize novel system designs and software methods that enable scientific laboratories to significantly increase the productivity of their drug discovery process; increase time for researchers to focus on core work and reduce time on repetitive surgical tasks; decrease labor costs, one of the largest components of the total laboratory costs, by paying lower wage workers to run these automated devices and reducing the time to perform the disclosed processes (e.g., sample collection and storage); maximize the accuracy of laboratory results and minimize human errors; provide data longevity, allowing for protection and tracking of the entire history of surgical data; enhance precision for drug delivery, reducing supply costs that arise from wastage; and overcome shortages in skilled scientific personnel, especially in developed countries.

The presently disclosed system provides a self-contained research platform comprising sensors combined with robotic assisted devices, tube handling/storage systems, anesthesia/euthanasia chambers, and robotic arms to conduct surgical procedures. The presently disclosed system further provides computer vision algorithms, and coordination of those algorithms with robotic hardware to execute tissue sampling and extraction, among other surgical procedures.

Figure 1B:
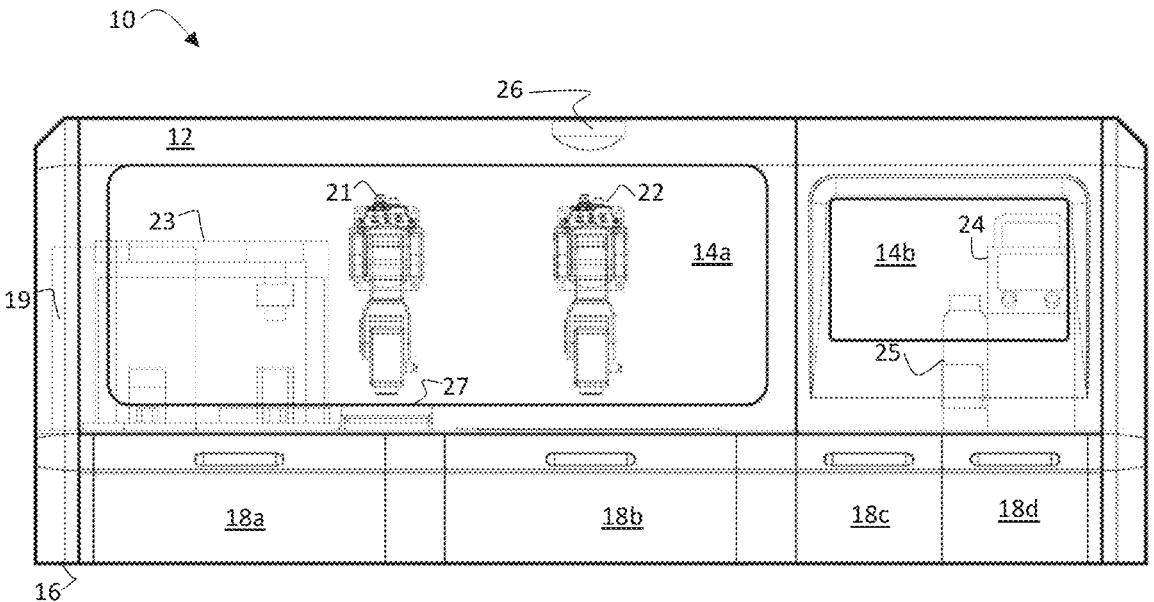
FIG. 1B illustrates a front view of the modular surgical system of FIG. 1A, wherein certain internal components are shown.
Figure 1C:
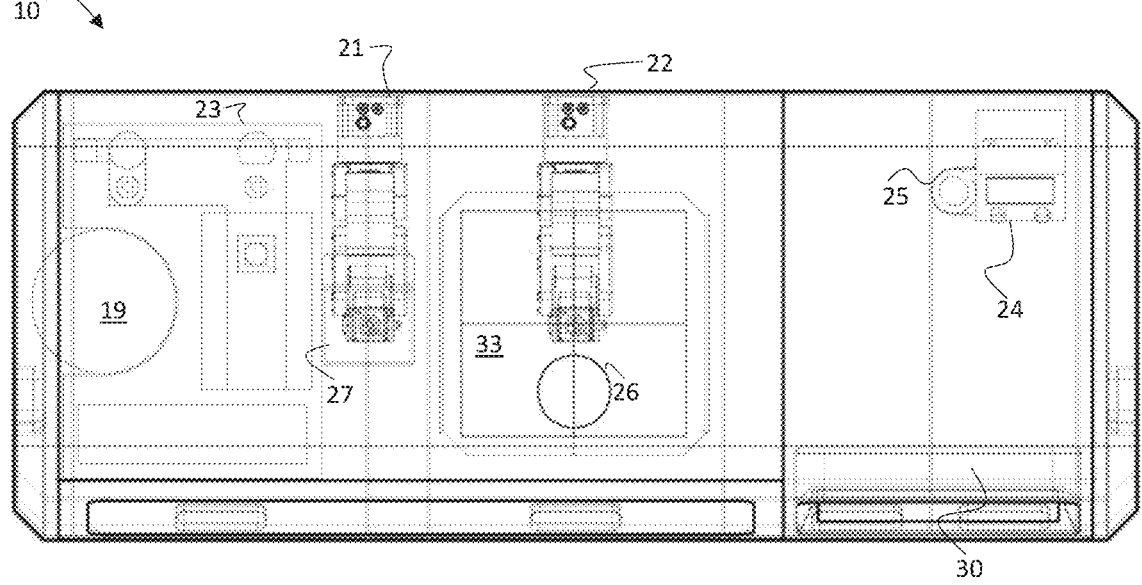
FIG. 1C illustrates a top view of the modular surgical system of FIG. 1A, wherein certain internal components are shown.

As shown in FIGS. 1A through 1C, the modular system 10 may include multiple interior hardware components that are surrounded by a frame 12 and enclosed by an exterior cover 14a. Stands or feet 16 may be included on the bottom of the frame 12 to ensure the system 10 is level prior to conducting surgical applications.

Exemplary interior hardware components include a freezer component 19 and a sample tube handling and labeling component 23, a robotic arm (two are shown in the figures; 21, 22), an analytic scale 27, an anesthesia/euthanasia chamber 29, a surgical platform 33 with a waste disposal system, and concealed areas that house electronic components 30. Exemplary exterior hardware components include drawers for sample storage 18a, biohazard waste storage 18b, and specimen input (18c-d), a user interface such as a touch screen panel 14b (see also FIG. 4), and dual side doors (41a, 41b) for material input (e.g., sample tubes, anesthesia, liquid nitrogen).

Figure 3:
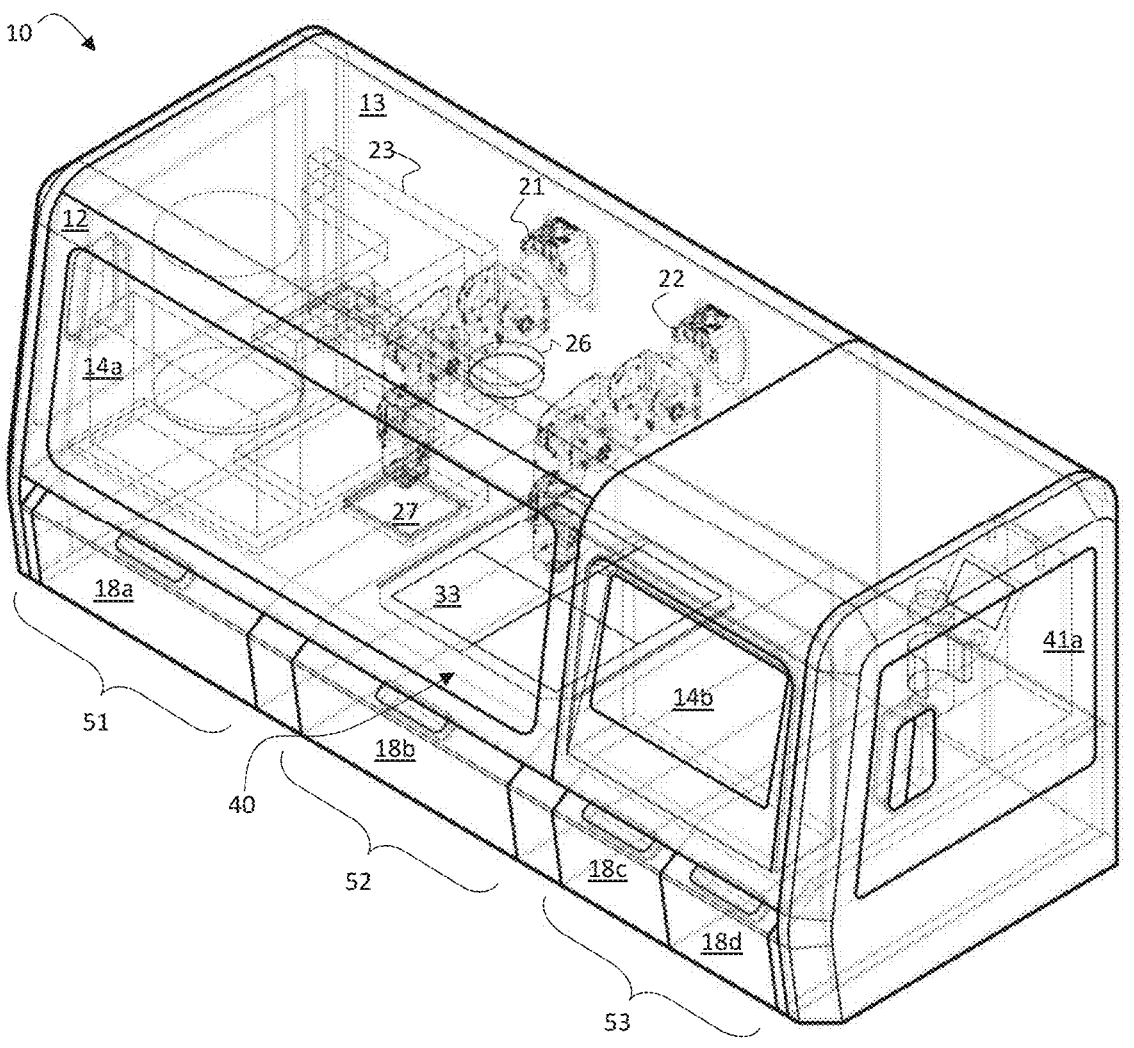
FIG. 3 illustrates a perspective top-down view of the modular surgical system of FIG. 1A, highlighting internal and external components of the system.

These exemplary components may be housed within individual systems or a single system. For example, these exemplary components may be compartmentalized so that they may be provided as individual units that may be combined to form the system 10. With reference to FIG. 3, the components may be compartmentalized into units such as a sample handling unit 51, a robotic surgical unit 52, and an anesthesia unit 53, wherein certain additional functionalities may be included with one or more of these units, such as a sample disposal unit 40 and a visual coordination unit 26. Together these components and/or units can perform common rodent surgical procedures such as drug implantation, injections, tissue excision, and device implantation with high accuracy and throughput as compared to unassisted surgeries.

With specific reference to FIG. 1C, which illustrates a top view of the modular surgical system 10, a hard exterior frame 12 is configured to surround an internal frame 13. The back of the exterior frame 12 is substantially flat and may afford benchtop accessibility with removable or openable exterior covers (14a, and 41a, 41b shown in FIGS. 2A and 2B) that allow for ease of changing internal components of the system. Moreover, such a design allows the modular surgical system 10 to fit against a wall inside of a laboratory, such as against a wall while resting on a benchtop. One layer internally, i.e., the internal frame 13, may be configured as a second wall spaced apart from and inward from the exterior frame 12. The space between the internal frame 13 and the exterior frame 12 may be configured to contain wiring and other components so that the system 10 provides a clean surgical area free from extra wires, as well as an aesthetically preferential look on the inside.

The internal frame 13 provides support for the robotic arms (21, 22), as well as for the laboratory sample handling devices 23. At least in the region of the robotic arms (21, 22), additional support members, e.g., steel frames, and panels may be included to provide a waterproof area that may be easily sanitized. For example, additional panels may be included on a back wall of the system 10, such as behind the robotic arm (two are shown in the figures; 21, 22), or on the back wall of the robotic surgical unit 52., or across a full length of the back wall inclusive of portions of the side walls.

Figure 2A:
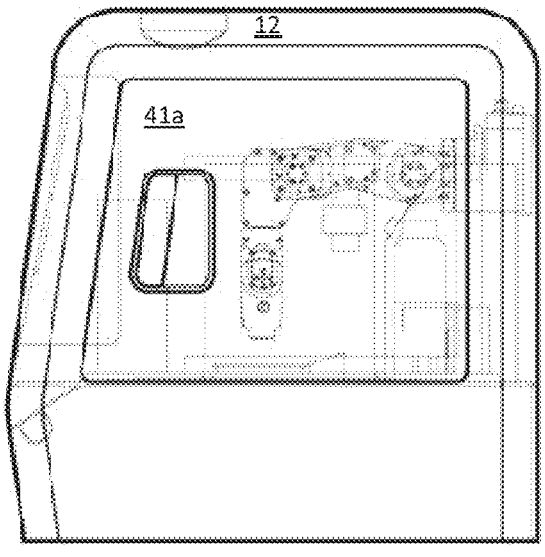
FIGS. 2A and 2B illustrate right- and left-side views, respectively, of the modular surgical system of FIG. 1A, wherein certain internal components are shown.
Figure 2B:
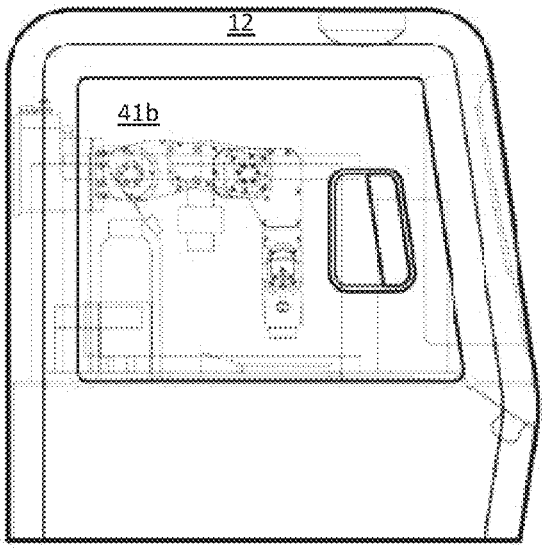

FIG. 2A depicts the right side of the presently disclosed invention and FIG. 2B depicts the left side. Each of these sides may include doors (41a, 41b, respectively) that can be opened to exchange interior consumable components for the anesthesia unit, tube labeling unit (i.e., sample handling unit), biohazardous waste, and surgical accessories. On the right side of the frame (FIG. 2A), the user interface devices and other robotic controllers may be positioned behind another removable plate allowing for easy access to the devices for troubleshooting or repairs. For example, a portion along a roof area of the system on the right side thereof may include an additional panel that houses electronic components. The panel may be configured as an access panel or door. Alternatively, or additionally, the user interface devices and other robotic controllers may be positioned behind the user interface panel 14b, which may be configured as a panel that opens to provide access therein.

With reference to FIG. 3, a top-down perspective view of the system is provided. The doors (14a, 41a, 41b) on the exterior face at the front and sides of the system 10 allow for easy access into the surgical plane inside of the device and/or for reloading of specific consumable surgical instrument accessories. The front door 14a may be configured to open away from the device (up) as shown in FIG. 1A, allowing the user to interact with the internal components, as necessary. According to certain aspects, the doors may lock upon the start of the surgery and cannot be opened while a surgical protocol is active.

Robotic Surgical Unit

The robotic surgical system 52 may comprise three main components: an articulated robotic arm (two are shown in the figures; 21, 22) and a surgical platform. The surgical platform 33 may include heating elements to maintain a stable and constant temperature of the animal. The surgical platform 33 may comprise a motorized component allowing for opening and closing, i.e., breakaway plate, such as opening into a waste disposal area (region defined by drawer 18b).

The robotic surgical unit 52 generally comprises the largest area within the center of the system 10. Each of the articulated robotic arms may contain a self-enclosed controller system and swappable end effectors for manipulating different substances or for performing different procedures. That is, a first end portion of the articulated robotic arm may have an end effector that contains multiple swappable devices, tools, or other surgical instruments. Each robotic arm may be equipped with an end effector that includes a plurality of "tools" and the ability to interchange these tools for new tools, i.e., when disposable such as scalpel blades, etc., or for different or clean tools during the surgical process.

Alternatively, or additionally, a first end portion of the articulated robotic arm may be configured to accept and exchange end effectors, e.g., tools, cleaning instruments, or other surgical instruments. This exchange may be manual, semi-automatic, such as via instructions from a user interface, or autonomous, such as programmed in a protocol or based on data from one or more sensors. Exemplary end effectors include a gripper, scalpel, pair of scissors, loop, electromagnetic end effector, electro adhesion end effector, a surgical instrument as otherwise defined hereinabove, or a combination thereof, i.e., the end effector may comprise multiple surgical and/or cleaning instruments that may be individually moved into a working position. Additionally, there may be an end effector depo, such as positioned at either side of the surgical platform 33, on a wall to which the robotics arms are attached (e.g., back wall), etc.

The robotic surgical unit 52 may further include a conveyor system inside of the large main chamber. The conveyor system may move the specimen into place within the surgical chamber, such as from the induction chamber of the anesthesia unit 53 to the surgical platform 33.

The robotic surgical unit may undergo a self-calibration prior to each surgical procedure (i.e., pipeline), and the unit may be "digitally" actuated during surgery at greater than 0.005 mm precision using colorimetric, spatial, and visual machine learning models. Calibration may be via specific references, such as visual markers (color, size, shape, etc.) used by cameras or visual sensors, weights used by the scale, secondary thermometers, etc. Additionally, specific surgical platforms may come equipped with warming centers (e.g., heating elements and sensors) that monitor the animal's temperature during a surgical procedure and offer real time heating for preventing decreased body temperature during these surgical techniques.

The system 10 may include a controller having a memory component, a storage component, and a compute component for running the system. Together, these components accelerate computations and workloads while offering a local storage of data. In certain configurations, the memory component may be integrated into a single board computer (SBC) such as edge devices and contain DDR3, DDR4 or DDR5 ram. The compute component may include up to three separate SBCs each with their own processor for running tasks within the system 10, including displaying the graphical user interface on an output device (user interface 14b). The storage component may include physical storage device including but not limited to a solid-state hard drive, SD cards, and removable flash storage devices. Together these components may enable local processing on the device, and communication with the cloud interface.

Visual Coordination System

Throughout the present disclosure, the visual coordination system is described as comprising sensors such as a multi-level camera tracking grid, multiple cameras, and integrated lighting. The visual coordination system may actively monitor the progress of the surgical procedure during and optionally thereafter, movement of the animal through the various stages of the procedure (i.e., on a conveyance system), and collection of the organs including weighing each organ to ensure success during every step of the surgery. The multi-level tracking grid may include multiple cameras that calculate the precise geospatial coordinates of the animal inside the device in real time. This multi-level system may integrate with the robotic surgical unit to provide input coordinates to facilitate the movement of the articulated robotic arms. The visual coordination system may include specific functionality, such as described and shown in FIGS. 6-10F. It should be understood that the presently disclosed visual coordination system is not limited to the exemplary functionality specifically shown herein.

Figure 6:
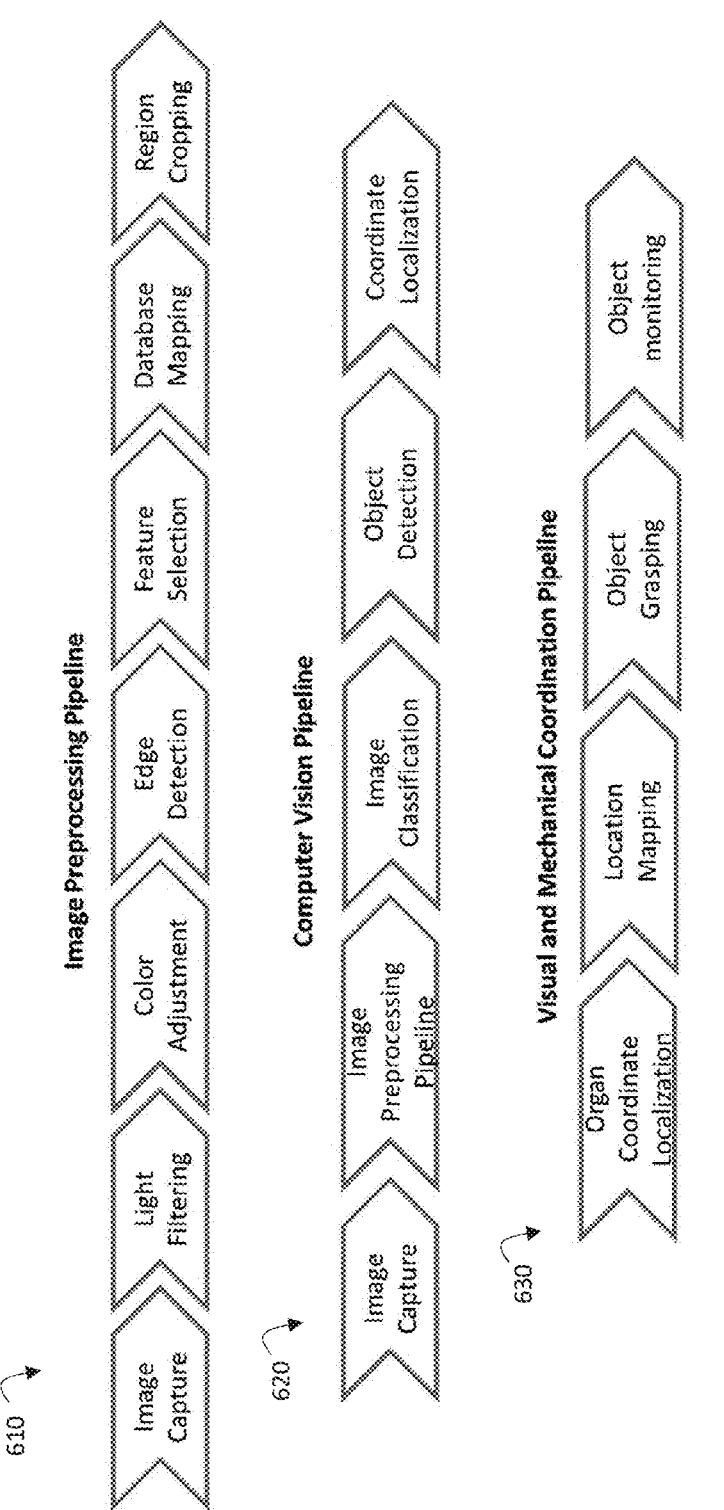
FIG. 6 is a diagram depicting robotic manipulation utilizing a visual coordination system and steps outlined in visual coordination workflows according to aspects of the present disclosure.

A computer vision workflow of the present disclosure may follow but is not limited to the steps outlined in FIG. 6. The computer vision system may follow a process whereby images are collected via the visual coordination system and real time data streams are processed for each surgery independently, allowing for precise control over the robotic coordination unit (e.g., visual coordination unit 26).

The computer vision workflow can be broken down into three main aspects: 1) a color-based workflow 610, 2) a machine learning workflow 620, and 3) a coordinate mapping workflow 630. The color-based workflow, i.e., image preprocessing pipeline 610, can be described as multiple sequential steps with optional intermediate actions, where traditional steps of image capture, color filtering (e.g., light filtering), light enhancement (e.g., color adjustment), regional cropping (e.g., edge detection), and masking (e.g., feature selection, database mapping, and region cropping) may be applied to each frame to accurately identify each organ system and its corresponding location within the surgical plane. Each frame is mapped to a corresponding physical location within the surgical plane and translated from pixel level values to coordinates with a unique mapping strategy.

The machine learning workflow, i.e., computer vision pipeline 620, may occur in parallel or sequentially with the color-based workflow, where a pretrained computer vision model that has been trained on a proprietary customized surgical dataset, analyzes an image to provide multiple outcomes including but not limited to image segmentation, object detection, object localization, image classification, and instance segmentation. There may also be a coordinate mapping workflow, i.e., visual and mechanical coordination pipeline 630, whereby results from the color-based and computer vision workflows are aggregated in a unique manner to map pixels to physical animals/organs and translate the steps necessary for the articulated robotic arms to conduct surgical applications.

Figure 7A:
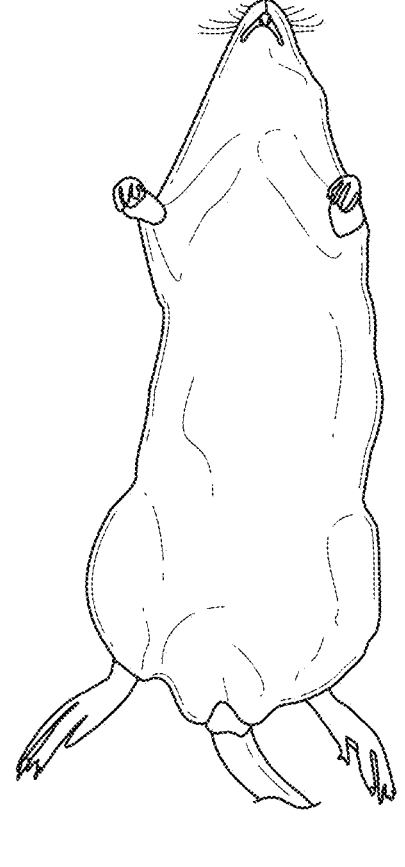
FIG. 7A depicts an image of a model animal captured by the disclosed system.
Figure 7B:
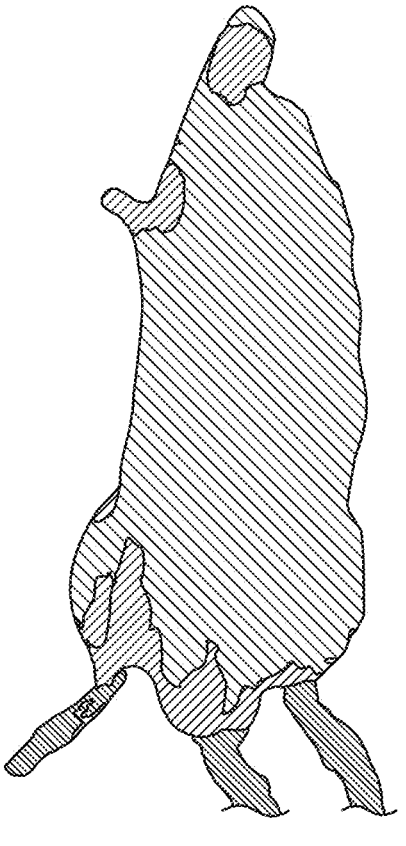
FIG. 7B provides a visual example of the machine learning detection and extraction of foreground objects alongside pre-segmented-areas for surgical applications according to aspects of the present disclosure based on the image of FIG. 7A.
Figure 8:
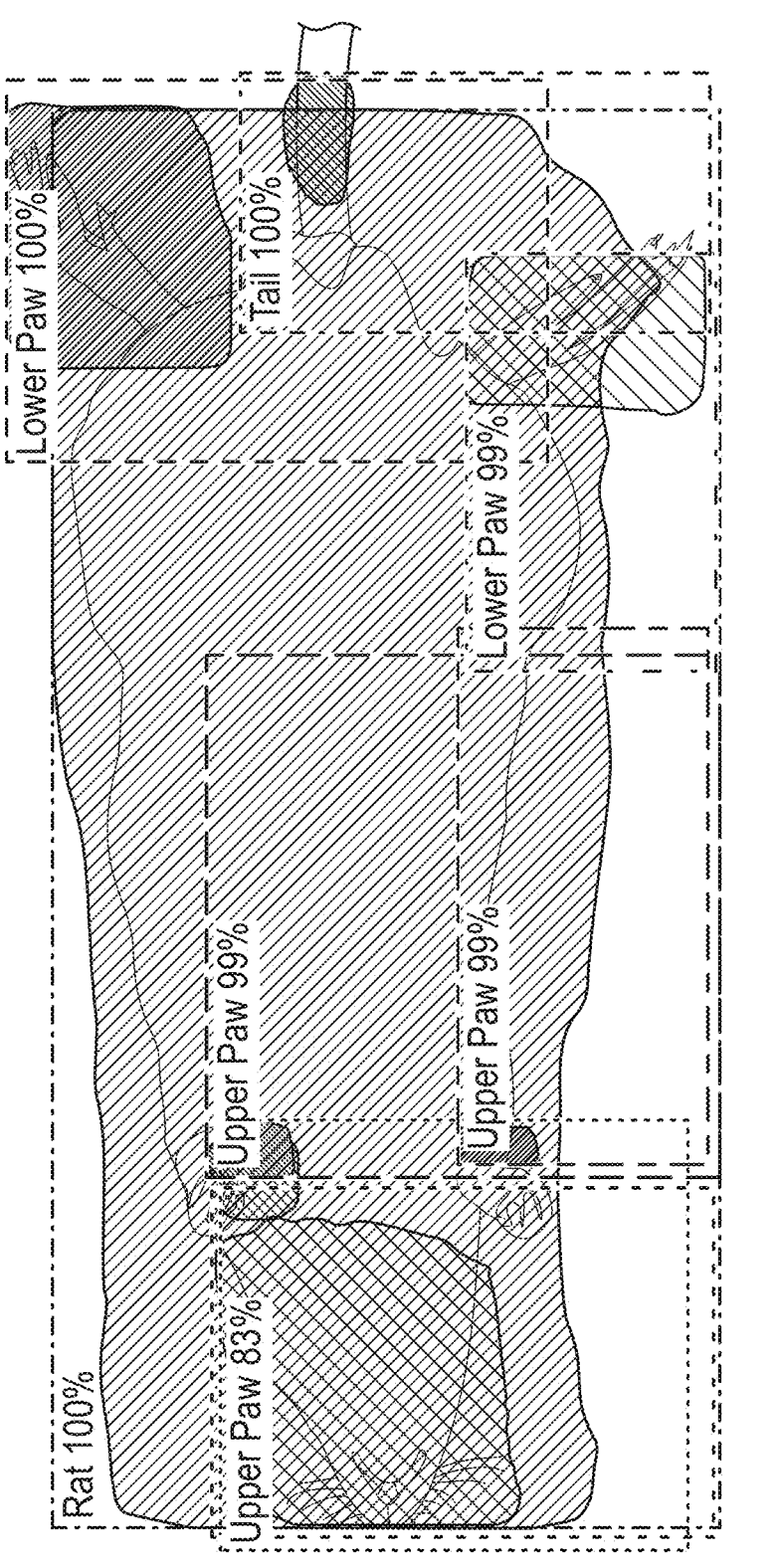
FIG. 8 represents an example of a computer vision system detecting surgical landmarks in an example rodent according to aspects of the present disclosure.

The computer vision workflow may also comprise multiple intermediate steps that are illustrated in FIGS. 7A and 7B, whereby images are subjected to foreground segmentation to extract the most important image details prior to passing through the color-based workflows. Additionally, the computer vision workflow may also contain a custom trained computer vision model capable of performing on external features as depicted in FIG. 8. Prior to surgical applications, these external features may be used to guide the robotic arms for positioning, such as prior to surgical instantiation, and these features may also be communicated through sensors in the surgical area. The multitude of sensors provide signals for the localization, detection, classification, and identification of the model organisms, and signals to the robotic manipulators to control the articulated arms. The sensors may also provide unique information about the depth, color, and necessary information to communicate with the visual communication system. Exemplary sensors include cameras (3D and color), Time-Of-Flight sensors, LIDAR systems, infrared sensors, magnetic sensors, or structured light sensors, or any other sensors known in the art and combinations thereof.

Figure 9:
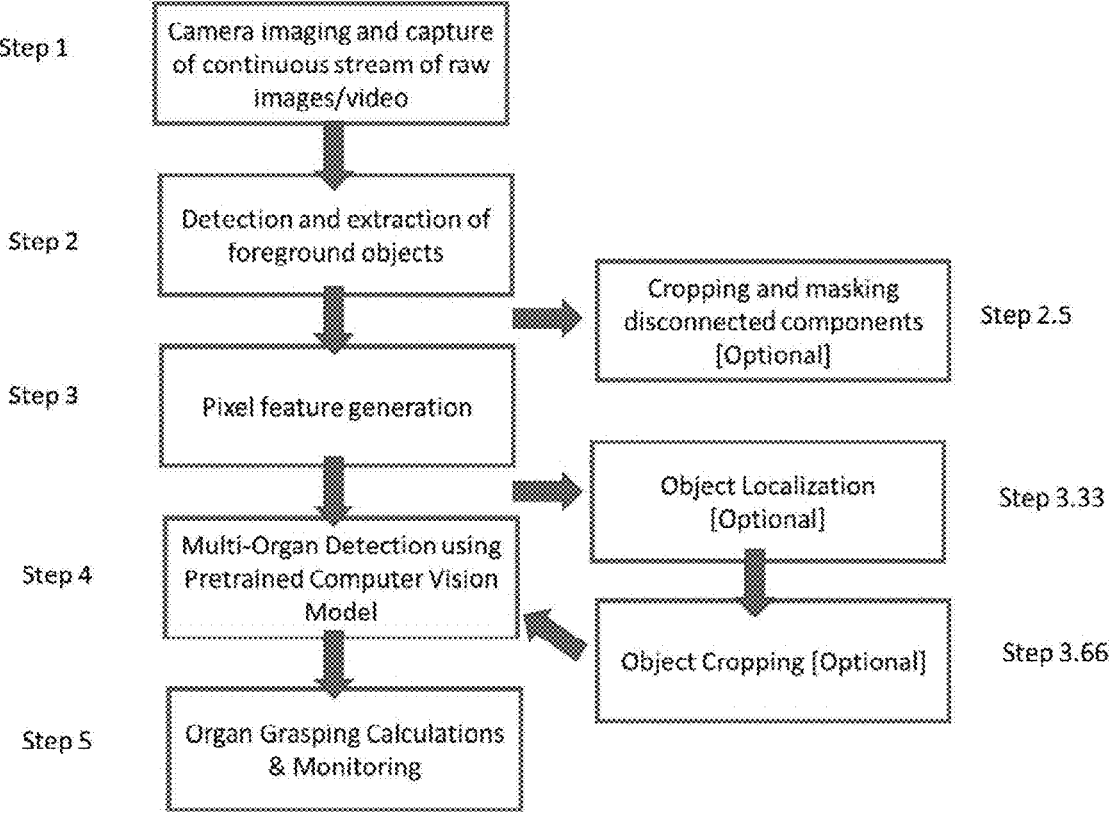
FIG. 9 depicts a flow diagram of the workflow process for pixel level and color level analysis of real-time video to perform surgical object detection alongside localization according to aspects of the present disclosure.
Figure 10B:
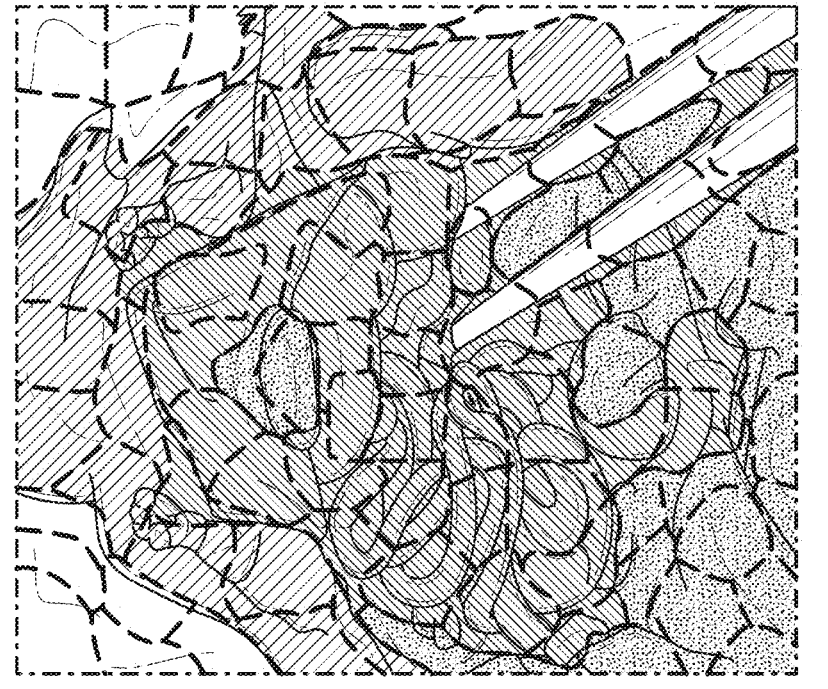
Figure 10A:
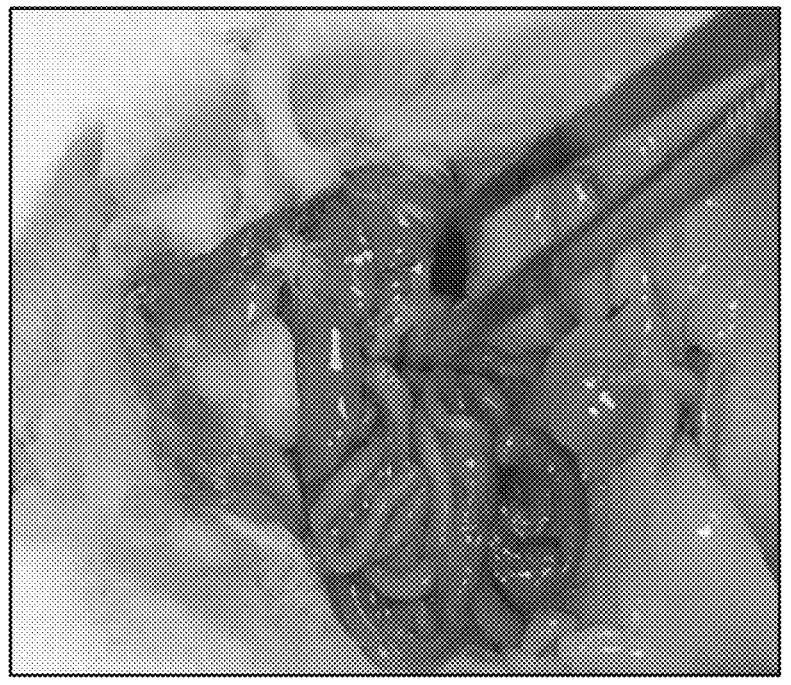
Figure 10D:
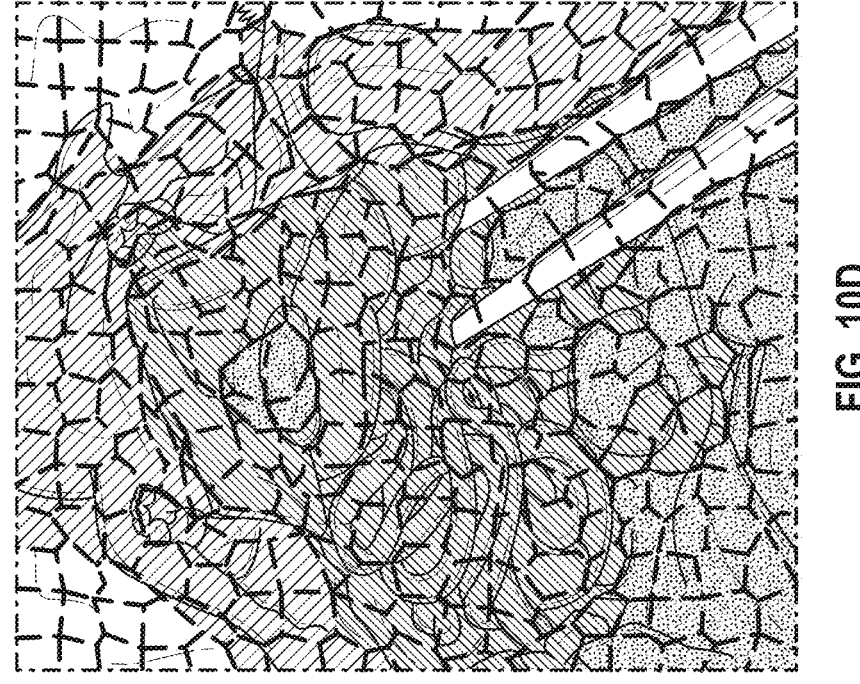
Figure 10C:
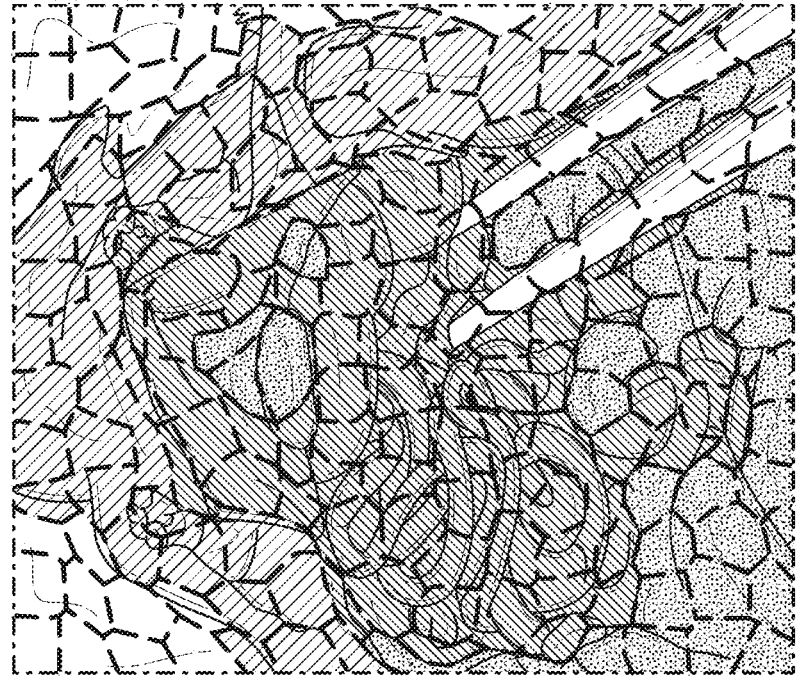
Figure 10F:
Figure 10E:
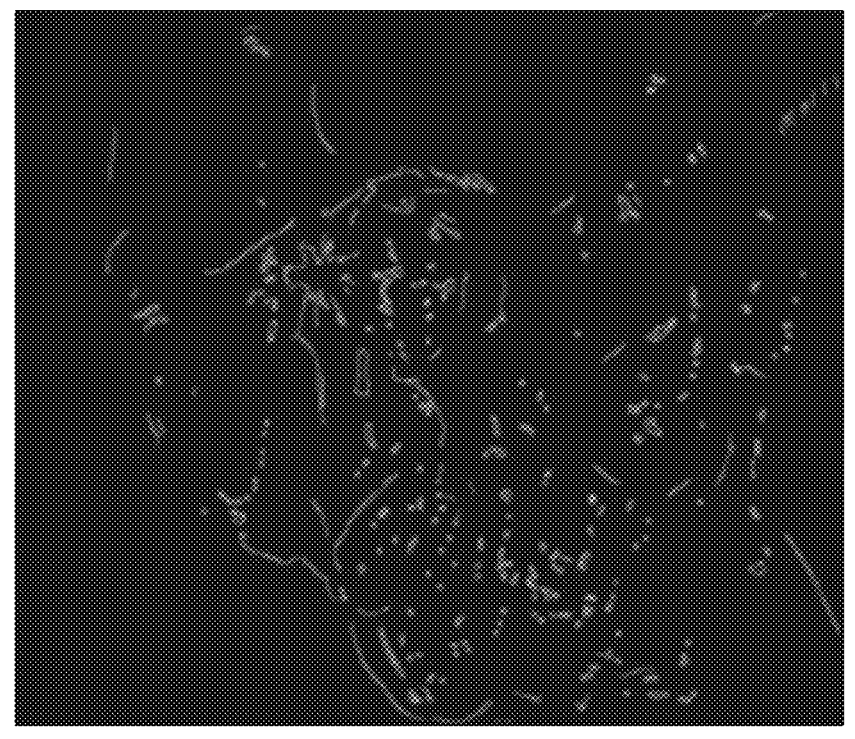

The computer vision workflow may follow a sequential step-by-step protocol as shown in the flow diagram in FIG. 9. This step-by-step process may occur in some renditions of the devices or follow a combination of the steps outlined in the diagram. As shown in FIG. 9, a first step (step 1) in the protocol may comprise imaging and capture thereof of the image data (i.e., continuous stream of raw images and/or video capture by a camera). This data is then used to detect and extract any foreground objects in the image data, shown as step 2 in FIG. 9. Optionally, disconnected components found in the image data may be cropped and/or masked (step 2.5). Step 3 of the protocol includes pixel feature generation followed by multi-organ detection using a pretrained computer vision model (step 4). Optionally, after step 3, objects may be localized in the image (step 3.33) and cropped (step 3.66), and this data may be provided as an input to step 4 (multi-organ detection). Finally, in step 5, calculations are made regarding use of the articulated robotic arm to grasp the organ or issue, and the process is continuously monitored during grasping of the organ/tissue by the articulated robotic arm.

Figure 11:
FIG. 11 provides an example containing multiple organ detection within a single frame.

Additional steps in the computer vision workflow may take place as the machine learning models are further trained on new surgical data under different conditions. During the computer vision workflow, features are generated from each individual frame to create several custom algorithms to aid in selecting the features of the image that are sent to the computer vision model as shown in FIGS. 10A-F. The resulting features that are generated by applying these algorithms may create numerical vectors of data that may be passed into the machine learning model to identify specific areas on each frame of the video that need to be translated to pixel coordinates for controlling the articulated robotic arms. An example of an input image that would undergo feature extraction is detailed in FIG. 11.

Figure 12B:
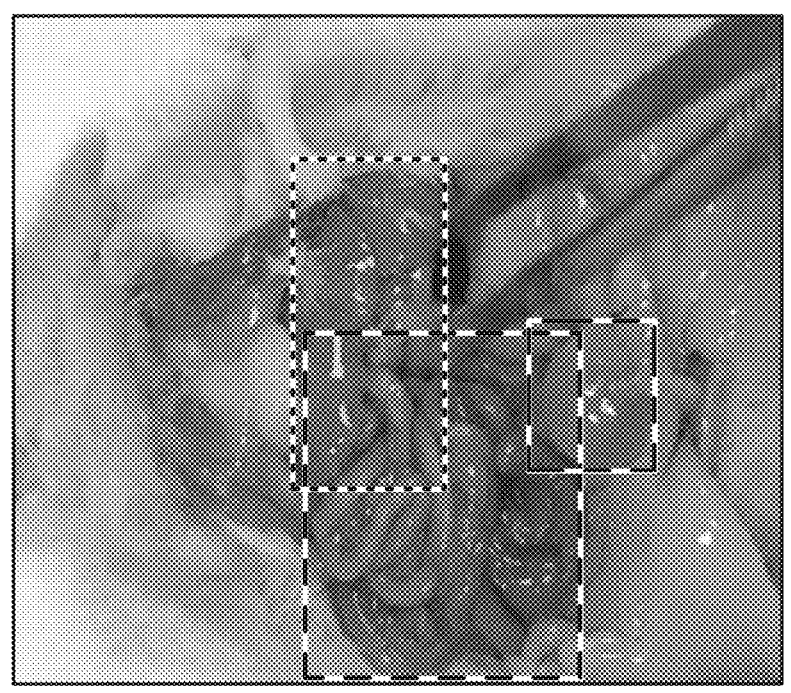
Figure 12A:

The performance of the computer vision models may be optionally enhanced by providing additional labeled training data to the computer vision system by participating in a labeling process on the user's local device. This process can be completed during a surgery or at any time while eligible data exists on the user's edge device. The customized training process may appear on the user interface device (e.g., touch screen 14b) of the system or can be interacted with via a remote cloud platform. An example of a user interface for providing customized feedback is shown in FIGS. 12A and 12B.

Thus, the present disclosure further provides methods for optimizing a future surgical procedure. The method may include providing, via a remote server or a user interface on the system, a selection of initial plans for a surgical procedure and surgical specimen, such as any of the procedures and specimens indicated herein (e.g., necropsy on a rat), and providing the selected initial plan to the system 10 (e.g., at least controllers for the articulated robotic arms). The method may further comprise sending, during and/or after the surgical procedure, to a remote server or the processor on the system information regarding the surgical procedure from the user and/or from the system. This information regarding an actual procedure may be used to create an initial plan for a subsequent surgical procedure that shares common features (i.e., type of procedure, surgical specimen).

An algorithm of the present disclosure may create the initial plan for a subsequent surgical procedure, which may include an aggregation of initial plans, surgical measurements, and numerical vectors of data stored on the server (local or cloud-based) from prior surgical procedures. Analysis of the aggregated data may be via known machine learning, reinforcement learning, or artificial intelligence methods and algorithms.

Biohazard Waste Disposal System

The biohazard waste disposal system may comprise a set of manual doors, a disposal bin, a resting chamber, a motorized bagger accessory, biohazardous waste container, and a sanitation system. Based on a user's selection at the start of the surgical protocol, such as via the graphical user interface (e.g., touch screen 14b), at the end of each procedure the animal may either be placed into a biohazardous waste container if performing an end-of-life procedure or moved into a resting chamber for retrieval after waking from the anesthesia. The disposal bin may comprise a box containing a removable drawer with an opening above to the surgical platform 33 (e.g., breakaway plate) that is directly connected to the sanitation system. The sanitation system may contain a network of tubes for spraying sanitation spray on the surgical platform and cleaning instruments. The sanitation system may contain refillable bottles for the user to insert into the system with clean water and/or other cleaning agents, and removable bottles for disposing biohazardous waste. The motorized bagger accessory may include a motorized component to move plastic waste disposal bags in place for collection of waste from the surgical applications.

The waste disposal system on the exterior face may be comprised of a larger drawer that pulls out towards the user and away from the device (e.g., 18b). The waste disposal system may allow for automated disposal of carcasses or biohazardous waste collected during a surgical protocol into clean biohazard waste bags that can be collected into the waste area so that multiple surgeries can be performed sequentially. While the biohazard waste disposal system has been described herein as a drawer configured to accept liquid and solid biohazardous waste, other configurations are within the scope of the presently disclosed invention. Moreover, different configurations of the biohazard waste disposal system may be included with different versions of the presently disclosed system, e.g., a system comprising only one unit (i.e., surgical, anesthesia, sample handling, etc.) or a system comprising multiple units.

Anesthesia Coordination Unit

An anesthesia system or anesthesia coordination unit may comprise a positive air-flow chamber, i.e., induction unit, a conveyor system, a sensor, a gas regulation controller, and automatic doors. An induction chamber is used to confine the animal in a closed space during anesthesia procedures. Exemplary chambers include an automatic lid or door that opens for entry and removal of the animal and closes to contain the animal and anesthesia gases, and two separate inlet and outlet openings for the entry of fresh anesthetizing gas and collection of scavenging waste gas material.

The anesthesia unit may provide multiple options for the user to select approved anesthesia based on their research institution guidelines and provide anesthesia/euthanasia via an induction chamber. The anesthesia coordination unit may allow a user to provide replaceable bottles of anesthesia, e.g., isoflurane. When configured as an induction chamber, the gas regulation controller may provide positive airflow to force the anesthetic into the induction chamber, displacing other gases and facilitating the animal to succumb to the anesthetic. The gas may be passed through a gas regulation controller and the gas chamber may be connected to a conveyor system allowing the animal to be transported into the main surgical area.

According to certain aspects, the system 10 may be configured to accept the animal for a surgical procedure through a drawer (18c, 18d) positioned adjacent the anesthesia/euthanasia chamber (i.e., the anesthesia unit 29), enabling a user to place the animal into the internal anesthesia/euthanasia chamber. The drawers operate on a sliding mechanism that allows the user to pull the drawer toward them, away from the surgical platform, and lift a lid such that a rodent can be placed inside of the drawer. Once the rodent has been placed securely inside of the drawer, the lid can be closed and the drawer can be pushed toward the device, flush with the face of the surgical platform. Additionally, buttons on the front face of the device enable the drawers to automatically unlock and eject, allowing the user to also remotely monitor and track when drawers were opened as part of an integrated cloud platform. The anesthesia unit 53 may include an anesthesia/euthanasia chamber 29 (e.g., induction chamber), an anesthetic supply 25 (e.g., a gas cylinder), and a flow regulator 24 that includes a flow rate detector and solenoid controllers.

To coordinate the appropriate gas exchange, a multitude of sensors may be integrated in the gas chamber and throughout the rest of the device. The plurality of sensors may enable real-time communication and visualization of the surgical platform 33 (e.g., breakaway plate) either remotely in an online cloud platform or locally through the user interface (e.g., touchscreen 14b). The sensors may include visual, audio, haptic, pressure, temperature, and gas sensors. For example, the system 10 may contain sensors for the following real-time monitoring: surgical platform temperatures, freezing unit temperatures, anesthesia/euthanasia chamber gas flow rates, anesthesia/euthanasia chamber gas composition, visual light sensors, and infrared light sensors. These sensors throughout the interior of the system 10 may be controlled remotely through the cloud platform, or locally through the user interface. Each sensor may contain a specialized cover and housing that enables the devices to withstand the surgical environments inside of the surgical platform and still operate within normal limits. While certain sensors and configurations thereof have been described herein, other sensors and configurations are within the scope of the presently disclosed invention. Moreover, different configurations of the sensors may be included with different versions of the presently disclosed system, e.g., systems comprising one or multiple units.

Software and User Interfaces

Implementations of the presently disclosed system, including the surgical platform, sample handling, and anesthesia units, are described within the context of a device configured to perform various steps, methods, and/or functionality in accordance with aspects of the described subject matter. It is to be appreciated that the system including a computing device or computer system can be implemented by one or more computing devices. Implementations of the system and various components or units thereof can be described in the context of a "device configured to", wherein the term configured may be taken to mean that the device can implement computer-executable instructions that are executed to perform various steps, methods, and/or functionality in accordance with aspects of the described subject matter.

Figure 4:
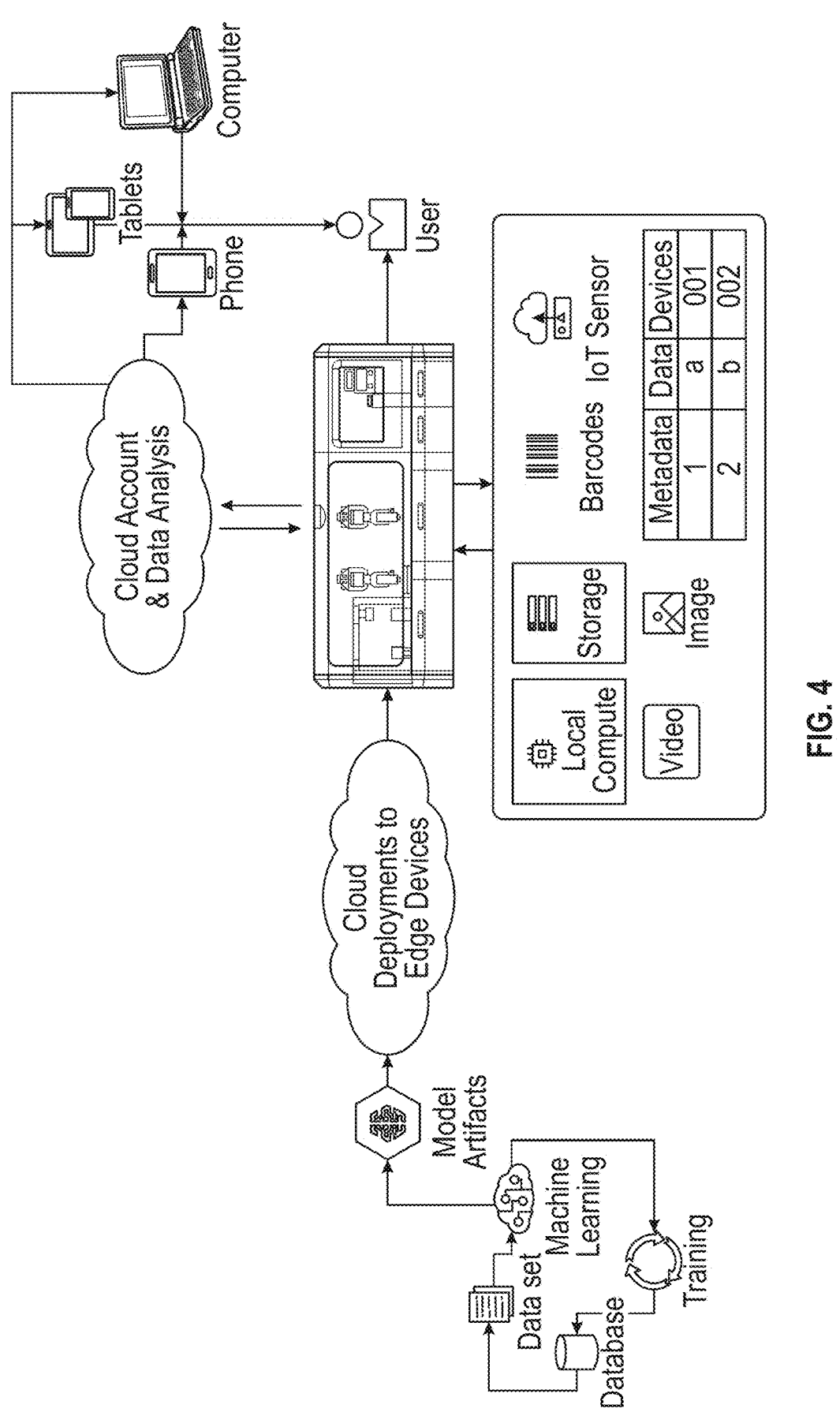
FIG. 4 is a diagram depicting a cloud server communication workflow that connects to edge devices according to aspects of the present disclosure.

In general, a computer system or computing device can include one or more processors and storage devices (e.g., memory and disk drives) as well as various input devices, output devices, communication interfaces, and/or other types of devices (see FIG. 4). A computer system or computing device can also include a combination of hardware and software. As such, it should be appreciated that various types of computer-readable storage media can be part of a computer system or computing device. As used herein, the terms "memory", "computer-readable storage media" and "computer-readable storage medium" do not mean and unequivocally exclude a propagated signal, a modulated data signal, a carrier wave, or any other type of transitory computer-readable medium. In various implementations, the robotic system and surgical platform may include a processor configured to execute computer-executable instructions and a computer-readable storage medium (e.g., memory and/or additional hardware storage) storing computer-executable instructions configured to perform various steps, methods, and/or functionality in accordance with aspects of the described subject matter.

Computer-executable instructions can be embodied and/or implemented in various ways such as by a computer program (e.g., client program and/or server program), a software application (e.g., client application and/or server application), software code, application code, source code, executable files, executable components, routines, application programming interfaces (APIs), functions, methods, objects, properties, data structures, data types, and/or the like. Computer-executable instructions can be stored on one or more computer-readable storage media and can be executed by one or more processors, computing devices, and/or computer systems to perform particular tasks or implement particular data types in accordance with aspects of the described subject matter.

The presently disclosed system can implement and utilize one or more program modules. Generally, program modules include routines, programs, objects, components, data structures, etc., that perform particular tasks or implement particular abstract data types. For example, the presently disclosed system includes at least an image processing module (see FIG. 6) that includes computer-executable instructions to interpret sensor signals for the localization, detection, classification, and identification of the model organisms, and send signals to the robotic manipulators to control the articulated arms.

The presently disclosed system can be implemented as a distributed computing system or environment in which components are located on different computing devices that are connected to each other through network (e.g., wired and/or wireless) and/or other forms of direct and/or indirect connections. In such distributed computing systems or environments, tasks can be performed by one or more remote processing devices, or within a cloud of one or more devices, that are linked through one or more communications networks. In a distributed computing environment, program modules can be located in both local and remote computer storage media including media storage devices. Still further, the aforementioned instructions can be implemented, in part or in whole, as hardware logic circuits, which can include a processor.

The presently disclosed system can be implemented by one or more computing devices such as computers, PCs, server computers configured to provide various types of services and/or data stores in accordance with aspects of the described subject matter. Exemplary sever computers can include, without limitation: web servers, front end servers, application servers, database servers, domain controllers, domain name servers, directory servers, and/or other suitable computers.

Components of the presently disclosed system can be implemented by software, hardware, firmware or a combination thereof. For example, the system can include components implemented by computer-executable instructions that are stored on one or more computer-readable storage media and that are executed to perform various steps, methods, and/or functionality in accordance with aspects of the described surgical procedures, visual detection, or machine learning.

The presently disclosed system can include a controller, memory, additional hardware storage, input devices, and output devices. Input devices can include one or more of the exemplary input devices described above, e.g., user interface, cloud platform, etc. Output devices can include data stored in a database, GUI output on the user interface, electronic or physical printed readout of procedure results or sensor values, and the like.

The presently disclosed system can contain one or more communication interfaces that allow the system to communicate with other computing devices and/or other computer systems. For example, and with reference to FIG. 4, the system may provide communication between a user interface, as accessed by the user, and a database on a local network (LAN) or across the internet. As such, the system may be provided locally or on a cloud-based system, or any combination thereof (i.e., run executable files locally using cloud-based data, or vice versa).

The presently disclosed system can include and/or run one or more computer programs implemented, for example, by software, firmware, hardware, logic, and/or circuitry of the sensors and/or robotics controllers. Computer programs can include an operating system implemented, for example, by one or more exemplary operating systems suitable for running on a computing device. Computer programs can include one or more applications.

The software to control the presently disclosed system may be displayed using a graphical user interface (GUI) to facilitate communication with the device (e.g., user interface). The GUI may include but is not limited to multiple screens for tissue selection, user account management and logging into the device, protocol selection and settings for controlling the surgical process. The GUI may be displayed on a user input device such as a touch screen or controlled through a remote computer over http communication. The local device inputs on a touch screen may also be integrated with various other hardware components for providing additional layers of security prior to accessing the surgical data on the machines, including integrations with key cards, USB password devices such as UbiKey, biometric scanners, or multi-factor authentication devices communicating with other personal electronics.

In addition to accepting the user input, the GUI may also integrate with the sensors that are contained throughout the device. The user interface may be a touch screen panel, USB inputs, a card reader, and buttons to accept the user input or control the physical device. The user may be able to control the device by following on-screen prompts through the touch screen and interacting with the buttons as directed.

The GUI on the touch screen may be configured to allow the user to monitor the status of the internal components locally or remotely through the cloud platform. To enhance the security of the device, locking mechanisms and user access control permissions may be available via multi-factor authentication protocols such as password protection, user account access controls, physical keycard or USB key locks, or mobile phone authentication.

The system is described as equipped with hardware allowing for communication with a remote cloud interface, such as shown in FIG. 4. A remote cloud communication interface may comprise multiple pieces of software and hardware combined to achieve this functionality. The user can interact with the system in multiple ways including but not limited to directly through the touch screen interface, connecting to the cloud platform either through a desktop or mobile version, or remotely in third party electronic lab notebook/laboratory information management system provider's software.

A remote cloud communication interface can be described as containing three key components: 1) a centralized cloud system, 2) local hardware interfaces including edge devices and an ethernet connection, and 3) a remote access platform. The centralized cloud system may be composed of systems designed to provision, deploy, update, and distribute firmware, software, or model updates remotely to edge devices over an ethernet connection. This centralized cloud system may be maintained at a site separate from the end user hardware, allowing for remote updates without requiring user interaction with the device.

The local hardware and edge devices are not limited to, but may contain, electronics for video capture, compute, memory, storage, user interface and visual displays either physically connected or able to communicate in a distributed fashion over a local network. A remote access platform can be described as a suite of software that enables the user to send commands to the hardware interface, and remotely control, download, upload, view, edit or manage their data/protocols over the internet. In the present disclosure, the remote access platform may contain multiple screens and websites that allow the user to interact with their device to examine data as depicted in FIG. 4.

Figure 5:
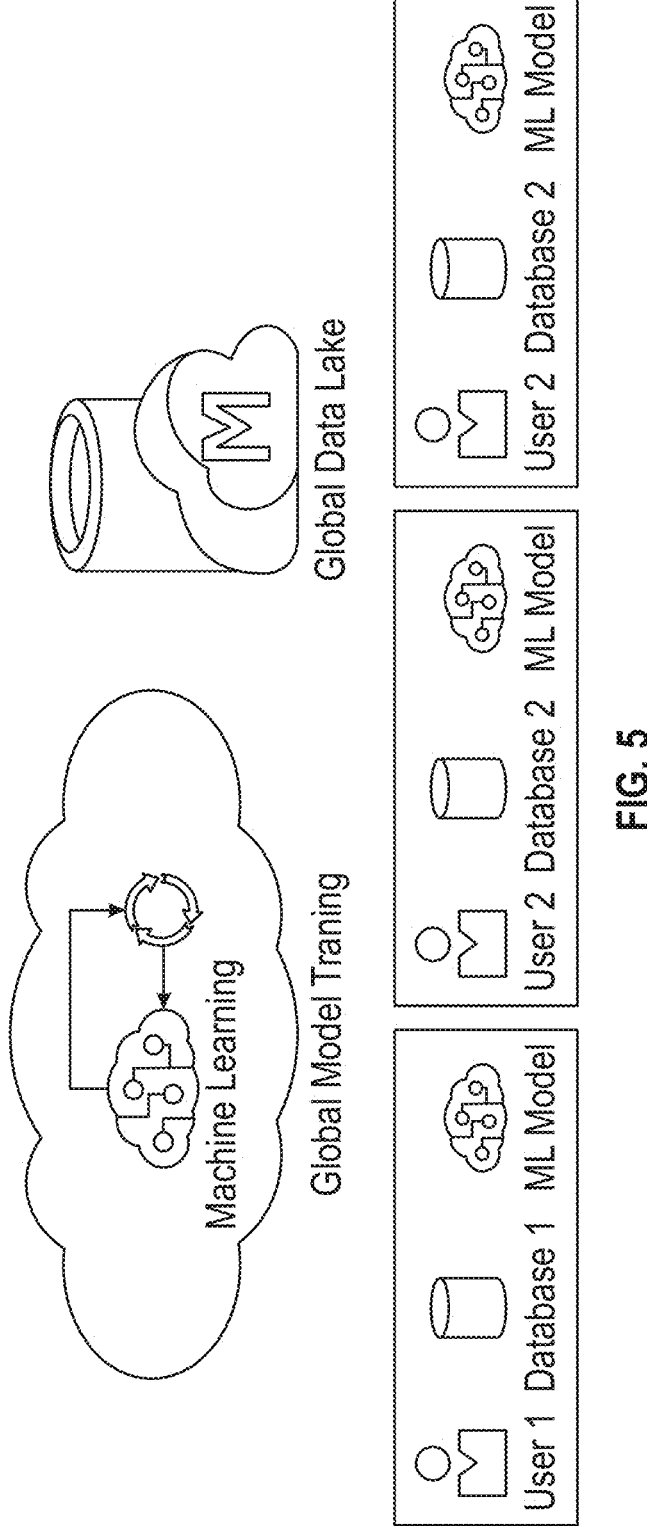
FIG. 5 is a diagram depicting the privacy aware machine learning infrastructure for communicating in federated environments according to aspects of the present disclosure.

The systems disclosed herein are depicted as equipped with hardware and software enabling privacy aware machine learning architectures to be utilized to ensure data privacy is maintained across the devices. As depicted in FIG. 5, users 1-3 would be able to maintain their data on local servers while a global model design in a central cloud hub would coordinate deployments to local edge devices. Each individual user would receive firmware updates from the central coordinating hub and retrain models on their individualized data, preventing unnecessary network traffic of the large video streams out of their network if needed. In this privacy aware architecture, users receive updated models based on their own data and area able to optionally provide data to enhance the global model through contributing to a managed cloud database with anonymous data contributors across any eligible edge device.

Sample Handling & Cryogenic Systems

The sample handling unit may comprise a multi-level storage rack, sample boxes, a labeling system, user provided sample tubes, a tube conveyor, and a cartesian robotic sample handling stage. The sample handling unit may mount to the wall of the housing, thus providing a platform for sample retrieval and a queue-based barcode sample tracking system. As shown in FIGS. 1-3, the sample handling unit 23 may be responsible for manipulating storage tubes that result from surgical procedures. These tubes may undergo labeling where a unique barcode may be applied to the exterior of the tube and each sample may be organized into a sample handling stage.

Each sample may be moved throughout the robotic system by a cartesian robot, which may open and close the tubes. Once a tube is filled with a sample, the tube may be closed and moved into the appropriate storage area as defined in the surgical protocol. The sample handling unit may move in an X-Y-Z 3-dimensional field and may closely interconnect with the tube conveyor and other exterior accessories that may be available. Additionally, there may be integrations with an analytical scale 27 for automatically recording sample weights immediately following excision, prior to being placed within a 1.5 ml tube.

The sample handling unit may comprise additional accessories, including but not limited to a tube hopper, a tube labeling apparatus, a tube rack, a tube opening device, a tube scanning device, and a tube organizing device. Each of these extensions may be integrated with sensors for digital tracking of the sample processing pipeline. The tube hopper may comprise an exterior shell and a mounting bracket, allowing for ease of connection between the exterior wall of the device for automating tube sorting. The tube hopper may comprise an internal auger that allows a user to insert empty 1.5 ml tubes and feed the tubes into the sample handling unit. The tube labeling apparatus may comprise a device allowing labeling of multiple or individual tubes once they have entered the device. The tube rack may comprise a frame with holes allowing samples to be organized within the device and the tube opening device may connect with the tube rack to open or close tubes. The tube scanning device may connect directly to the compute apparatus to scan unique identifiers on each tube for data management.

The cryogenic system may include but is not limited to a freezer component 19, a removable liquid nitrogen duer, and/or a sample freezing stage. The freezer component may be described as a compartment containing doors that allow sample boxes to be placed therein to stay cold. The liquid nitrogen duer may allow the user to provide liquid nitrogen to be used throughout the surgery to rapidly freeze tissues and a sample freezing stage may be used to rapidly cool down samples prior to freezing or be prepared to be placed within tubes prior to freezing. The cryogenic system may be directly attached to a wall of the sample handling unit 51 so that a user can open the door (e.g., 41*b*) to add liquid nitrogen and remove samples when a run is completed. Accordingly, the freezer component may include a door 41*b* on the exterior face to open for sample retrieval. The user may be able to either remove individual samples or groups of samples and may further allow the user to fill liquid nitrogen into a sample storage/freezing area.

Aspects of the Presently Disclosed Invention:

The presently disclosed robotic systems and methods enable a robotic arm with a high degree of freedom to manipulate common research tools (i.e., surgical instruments, grippers, cleaning tools, etc.) to perform tissue excision, collection, and storage. Each of these systems include one or more components that are individually configured to automate specific tasks related to the tissue excision, collection, and storage, such as small animal anesthesia/euthanasia, small animal surgery (e.g., tissue excision), and sample tube labeling and storage.

A system of the present disclosure may include a processor, a memory, a plurality of sensors, and a surgery unit comprising an articulated robotic arm comprising an end effector and a surgical platform. The processor may be coupled to a plurality of sensors and the articulated robotic arm, wherein a plurality of sensors provide signals related to detection and identification of features of a surgical specimen, and wherein the memory stores program instructions executable by the processor to process data received from a plurality of sensors and output control signals to the articulated robotic arm to perform an automated surgical procedure. The memory of the system may also include configuration files to run the robotic arms, allowing for successful calibration prior to each process execution.

The surgical platform may be integrated into a biohazardous waste system, or it may be separated for enhanced functionality. The surgical platform may comprise a breakaway plate configured to open to a collection chamber positioned there below. The collection chamber may be configured as part of a drawer on the system that collects waste into individual closable containers when the breakaway plate opens. The biohazard waste system may comprise a chamber capable of bagging samples and allowing the user to remove completed samples from the system. Further, this biohazard waste system may include a manipulation device to move biohazard bags for capturing discarded samples from the main surgical platform. The biohazard waste system may include a single movable drawer for users to manually remove samples without automated sample disposal.

The articulated manipulator arm may be capable of highly precise surgical tasks with a high-degree-of-freedom. Further, the first end portion of the articulated manipulator arm may have an end effector that contains multiple swappable devices, tools, or other surgical instruments, or that is configured to accept a tool or other surgical instrument. As such, the end effector may comprise any of a gripper, scalpel, pair of scissors, loop, electromagnetic end effector, electro adhesion end effector, a surgical instrument as otherwise defined herein, a cleaning tool, or a combination thereof. Alternatively, the end effector may be configured to accept any of a gripper, scalpel, pair of scissors, loop, electromagnetic end effector, electro adhesion end effector, a surgical instrument as otherwise defined herein, a cleaning tool, or a combination thereof. Additionally, or alternatively, the end effector may comprise a swap mechanism capable of changing tools. According to certain aspects, the end effector may comprise two or more tools or surgical instruments and may swap a first tool for a second tool, such as during a procedure. The tool swap may be manual, such as via real-time commands from a user interface, or autonomous. According to certain aspects, the articulated robotic arm may be configured to autonomously exchange tools. That is, the articulated robotic arm may remove a first tool from the end effector and insert a second tool in the end effector.

A system of the present disclosure may include a processor, a memory, a plurality of sensors, and an anesthesia unit comprising a positive air flow chamber, i.e., an induction chamber, an anesthetic supply, and a flow regulator in fluid communication with the anesthetic supply, e.g., a gas cylinder, and the induction chamber. The flow regulator may comprise a flow rate detector and solenoid controllers. The processor may be coupled to the flow regulator and output control signals to the solenoid controllers. The memory may store program instructions executable by the processor to process data received from the flow rate detector and a plurality of sensors to track progress of the anesthesia, to change a flow rate of the anesthetic from the anesthetic supply to the induction chamber, or both. When this system is included in a larger system comprising the surgery unit and components associated therewith, the system may include a conveyor system to move a surgical specimen from the induction chamber to the surgical platform. Furthermore, the anesthesia unit may be configured to have swappable components, such as components that allow use of either a gas or liquid anesthetic, and/or adjusting anesthesia and refilling the liquid chemicals for low flow anesthetic applications.

A system of the present disclosure may include a processor, a memory, a plurality of sensors, and a sample handling unit comprising a tube labeling system and a tube manipulation robot, wherein the tube manipulation robot is configured to collect sample tube from a tube container, place the sample tube into position within the tube labeling system, label the sample tube to provide labeled sample tube, and position the labeled sample tube for collection of a sample from the surgical specimen. The tube labeling system may be configured to mark the sample tube with a barcode, text comprising a sample name, a sample collection date, a sample collection time, a protocol name, a protocol number, a user identity, or any combination thereof. The sample handling unit may further include a sample storage area configured as a drawer on the system, wherein a temperature of the sample storage area may below −20° C., and the sample handling unit includes a freezing system comprising removable liquid nitrogen canister and/or an integrated liquid nitrogen refilling and dispensing station that is configured to provide refill of liquid nitrogen. The sample storage area may also comprise cooling unit configured to maintain samples placed therein at a user selected temperature. The memory may store program instructions executable by the processor to process data received from a plurality of sensors to track progress of the sample tube labeling and storage, and output control signals to the tube manipulation robot.

A system of the present disclosure may include any combination of two of the systems noted herein above. For example, the system may comprise a memory, a processor, a plurality of sensors, and any combination of two of a surgery unit, an anesthesia unit, and a sample handling unit.

A system of the present disclosure may include each of the systems noted herein above. For example, the system may comprise a memory, a processor, a plurality of sensors, a surgery unit, an anesthesia unit, and a sample handling unit. Such a system may include a conveyance device, e.g., a conveyor belt, that can transport samples throughout the system, such as from the anesthesia unit to the surgery unit.

A system of the present disclosure may include one or more sensors, a remote communication interface, a memory component, a processing component, one or more machine learning compute nodes, articulated manipulator arm, a visual coordination system, a sample handling system, a freezing system, a biohazard waste system, and a human interface system.

Each of the systems individually or collectively may be positioned within an interior of a housing having an inner shell, an outer shell, and an access door.

Each of the systems individually or collectively comprise a sensor or a plurality of sensors, wherein exemplary sensors include one or more of color cameras, 3D cameras, LIDAR systems, infrared sensors, time-of-flight sensors, magnetic sensors, force sensors, pressure sensors, structured light sensors, temperature sensors, humidity sensors, pressure sensors, gas sensors, and any other sensors known in the art that are useful for robotic manipulation and calibration, climate control, automated surgeries, and the like.

Each of the systems individually or collectively may comprise memory and processing components that may use system specific information such as calibration data to ensure proper performance of the system, i.e., data received from the sensor, computer programming instructions on the memory that are executed by the processor to run the system, sensor data regarding the system environment and status of the various processes.

Each of the systems individually or collectively may comprise a remote communication interface to communicate data collected by the various systems with a local server and/or a cloud computing environment. The remote communication interface may comprise a database for recording real-time data that may be collected from the various systems. The database may be a local database, a cloud-based database, or both local and cloud-based databases. The remote communication interface may be linked with the user input device to provide communication with the servers/database (i.e., local and/or cloud-based), thus improving security of the system or systems, allowing for shared use of the system or systems across multiple labs and badge-based security systems so specific users may or may not have access to aspects of the device. Additionally, the remote communication interface may enable users to not need to enter labels for tubes that can be handled remotely, while also managing processes on each system remotely. Small configuration files may be periodically shared with the database via the remote communication interface to track version configurations across processes for reproducibility. The communication between the system and the server/database may include either wired or wireless communication or a combination thereof.

Each of the systems individually or collectively may include a human interface system. The human interface system may comprise a graphical display monitor and an input device. The input device may be a touch screen or voice command interface, for the user to view displayed progress or information intended to direct the robot and display error information. Additionally, the remote interface may include additional features within the interface system giving the user control to access the cloud platform.

Each of the systems individually or collectively may comprise one or more machine learning compute nodes. A machine learning compute node contains trained machine learning model and a corresponding tensor processing unit with a central processing unit to run real time machine learning models. These compute nodes may comprise separate physical hardware to conduct the computations, or integrated electronic platform capable of running the device while simultaneously processing the machine learning calculations. The compute nodes may comprise cloud compute notes that do not require any physical devices connected to the machine.

A visual coordination system may comprise multiple visual sensors/tools including color cameras, 3D cameras, LIDAR systems, infrared sensors, time-of-flight sensors, structured light sensors, and the like. The visual coordination system may comprise lights that enable communication of visual information. Further, the visual coordination system may communicate with the central server either by wired, wireless networks or a combination thereof. Additionally, the visual communication system may contain swap ready pieces in a modular fashion enabling updated hardware concurrent with future firmware upgrades.

What is claimed is:

1. A system for automated surgical procedures comprising:

a processor and a memory;

an articulated robotic arm comprising an end effector;

a plurality of sensors;

a surgical platform;

an induction chamber;

an anesthetic supply; and a flow regulator in fluid communication with the anesthetic supply and the induction chamber, the flow regulator comprising a flow rate detector and solenoid controllers, wherein the processor is coupled to the flow regulator and outputs control signals to the solenoid controllers, wherein the memory stores program instructions executable by the processor to process data received from the flow rate detector and the plurality of sensors to track progress of the automated surgical procedure, to change a flow rate of the anesthetic from the anesthetic supply to the induction chamber, or both, wherein the processor is coupled to the plurality of sensors and the articulated robotic arm, wherein of the plurality of sensors provide signals related to detection and identification of features of a surgical specimen, and wherein the memory stores program instructions executable by the processor to process data received from the plurality of sensors and output control signals to the articulated robotic arm to perform an automated surgical procedure.

2. The system of claim 1, wherein the end effector comprises a surgical instrument or a cleaning instrument.

3. The system of claim 1, wherein the articulated robotic arm is configured to autonomously exchange the end effector for a second end effector, wherein the autonomous exchange of the end effector comprises removing the end effector and inserting the second end effector.

4. The system of claim 1, comprising two articulated robotic arms.

5. The system of claim 1, wherein the plurality of sensors comprise one or more of color cameras, 3D cameras, LIDAR systems, infrared sensors, and time-of-flight sensors; and one or more of temperature sensors, humidity sensors, pressure sensors, and gas sensors.

6. The system of claim 1, including a conveyor system to move the surgical specimen from the induction chamber to the surgical platform.

7. The system of claim 1, wherein the anesthetic supply is a gas cylinder.

8. The system of claim 1, wherein the surgical platform comprises a breakaway plate configured to open to a collection chamber positioned below.

9. The system of claim 8, wherein the collection chamber is configured as part of a drawer on the system that collects waste into individual closeable containers when the breakaway plate opens.

10. The system of claim 1, including a sample handling unit comprising a tube labelling system and a tube manipulation robot, wherein the tube manipulation robot is configured to collect sample tubes from a tube container, place the sample tubes into position within the tube labelling system to provide a labeled sample tube, and position the labeled sample tube for collection of a sample from the surgical specimen.

11. The system of claim 10, wherein the tube labelling system is configured to mark the sample tube with a barcode, text comprising a sample name, a sample collection date, a sample collection time, a protocol name, a protocol number, a user identity, or any combination thereof.

12. The system of claim 10, further including a sample storage area configured as a drawer on the system.

13. The system of claim 12, wherein a temperature of the sample storage area is below −20° C., and the sample handling unit includes a freezing system comprising removable liquid nitrogen canister.

14. The system of claim 13, wherein the freezing system further includes an integrated liquid nitrogen refilling and dispensing station that is configured to provide refill of liquid nitrogen.

15. The system of claim 12, wherein the sample storage area comprises cooling unit configured to maintain samples placed therein at a user selected temperature.

16. The system of claim 1, further comprising a remote communication interface, wherein the system is configured to send data collected during the automated surgical procedure to a remote server, receive data related to the automated surgical procedure from the remote server, store program instructions to the memory received from the remote server, or any combination thereof.

17. The system of claim 1, wherein one or more of the plurality of sensors comprises a camera configured to acquire images during the automated surgical procedure and transmit the images in real time to the processor, and the processor is configured to generate image data representing at least a part of the image.

18. The system of claim 17, wherein the processor is configured to determine a real-time spatial position of the end effector of the articulated robotic arm based on the image data.

19. The system of claim 18, wherein the end effector comprises a calibration location and the processor is configured to perform a calibration of the real-time spatial position of the end effector.

20. The system of claim 17, wherein the processor directs real-time positions of the articulated robotic arm and the end effector attached thereto during the surgical procedure based on machine learning applied to datasets of previously performed surgical procedures.

21. The system of claim 1, wherein the articulated robotic arm, the plurality of sensors, and the surgical platform are positioned within an interior of a housing having an inner shell, an outer shell, and an access door, wherein the articulated robotic arm is attached to a wall of the housing on the inner shell, and wherein access to the interior of the housing is via the access door, and wherein the processor outputs control signals to lock the access door during the automated surgical procedure.

* * * * *